(12) United States Patent
Cali et al.

(10) Patent No.: US 11,066,692 B2
(45) Date of Patent: Jul. 20, 2021

(54) REAL-TIME MONITORING

(71) Applicant: PROMEGA CORPORATION, Madison, WI (US)

(72) Inventors: James J. Cali, Verona, WI (US); Sarah Duellman, Fitchburg, WI (US); Jolanta Vidugiriene, Madison, WI (US); Wenhui Zhou, San Luis Obispo, CA (US)

(73) Assignee: Promega Corporation, Madison, WI (US)

( * ) Notice: Subject to any disclaimer, the term of this patent is extended or adjusted under 35 U.S.C. 154(b) by 203 days.

(21) Appl. No.: 16/137,832

(22) Filed: Sep. 21, 2018

(65) Prior Publication Data
US 2019/0010537 A1 Jan. 10, 2019

Related U.S. Application Data

(63) Continuation of application No. 14/038,438, filed on Sep. 26, 2013, now abandoned.

(60) Provisional application No. 61/705,993, filed on Sep. 26, 2012.

(51) Int. Cl.
*C12Q 1/66* (2006.01)
*G01N 33/50* (2006.01)

(52) U.S. Cl.
CPC ........... *C12Q 1/66* (2013.01); *G01N 33/5005* (2013.01)

(58) Field of Classification Search
CPC combination set(s) only.
See application file for complete search history.

(56) References Cited

U.S. PATENT DOCUMENTS

| | | |
|---|---|---|
| 2005/0026171 A1 | 2/2005 | Hawkins et al. |
| 2006/0073529 A1 | 4/2006 | Contag et al. |
| 2010/0281552 A1 | 11/2010 | Encell et al. |
| 2012/0107849 A1 | 5/2012 | Klaubert et al. |
| 2014/0099654 A1 | 4/2014 | Cali et al. |

FOREIGN PATENT DOCUMENTS

| | | |
|---|---|---|
| WO | 2001036617 | 5/2001 |
| WO | 2002099428 | 12/2002 |
| WO | 2004027378 | 4/2004 |
| WO | 2005003377 | 1/2005 |
| WO | 2007027653 | 3/2007 |
| WO | 2014052653 | 4/2014 |

OTHER PUBLICATIONS

Cali et al., Luminogenic cytochrome P450 assays, Expert Opin Drug Metab Toxicol. Aug. 2006;2(4):629-45.
Cali et al., "Bioluminescent assays for ADMET." Expert Opin Drug Metab Toxicol. Jan. 2008; 4(1)103-20.
Cali et a., "Bioluminescent assays for ADME evaluation: dialing in CYP selectivity with luminogenic substrates." Expert Opin Drug Metab Toxicol. Sep. 2012; 8(9):1115-30.
Jones et al., Releasable luciferin-transporter conjugates: tools for the real-time analysis of cellular uptake and release, J Am Chem Soc. May 24, 2006;128(20):6526-7.
Promega Corporation, ENDUREN Live Cell Substrate Technical Manual, Nov. 2011.
"Ready-To-Grow Secreted Luciferase Reporter Systems User Manual", Clontech Laboratories Inc. Jan. 2012, Version No. 011612, 17 pages.
Supplementary European Search Report for EP13841100.4, dated Apr. 22, 2016, 7 pages.
Santos et al., Sensitive in vivo imaging of T cells using a membrane-bound Gaussia princeps luciferase. Nat Med. Mar. 2009;15(3):338-44.
Hall et al., Engineered luciferase reporter from a deep sea shrimp utilizing a novel imidazopyrazinone substrate. ACS Chem Biol. Nov. 16, 2012;7(11):1848-57.

*Primary Examiner* — Heidi Reese
(74) *Attorney, Agent, or Firm* — Casimir Jones SC; David W. Staple

(57) ABSTRACT

Provided herein are methods for the real-time monitoring of an intracellular event or response. In particular, the methods provided herein monitor the conversion of a pro-substrate to a substrate for a protein sensor as a result of an intracellular event or response.

10 Claims, 26 Drawing Sheets

Specification includes a Sequence Listing.

SEQUENCE LISTING

<160> NUMBER OF SEQ ID NOS: 7

<210> SEQ ID NO 1
<211> LENGTH: 171
<212> TYPE: PRT
<213> ORGANISM: Artificial Sequence
<220> FEATURE:
<223> OTHER INFORMATION: Synthetic

<400> SEQUENCE: 1

```
Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60
```

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
            115                 120                 125

Val Thr Gly Thr Leu Trp Asn Gly Asn Lys Ile Ile Asp Glu Arg Leu
130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala
                165                 170

<210> SEQ ID NO 2
<211> LENGTH: 544
<212> TYPE: PRT
<213> ORGANISM: Photuris pennsylvanica

<400> SEQUENCE: 2

Met Ala Asp Lys Asn Ile Leu Tyr Gly Pro Glu Pro Phe Tyr Pro Leu
1               5                   10                  15

Glu Asp Gly Thr Ala Gly Glu Gln Met Phe Asp Ala Leu Ser Arg Tyr
                20                  25                  30

Ala Ala Ile Pro Gly Cys Ile Ala Leu Thr Asn Ala His Thr Lys Glu
            35                  40                  45

Asn Val Leu Tyr Glu Glu Phe Leu Lys Leu Ser Cys Arg Leu Ala Glu
        50                  55                  60

Ser Phe Lys Lys Tyr Gly Leu Lys Gln Asn Asp Thr Ile Ala Val Cys
65                  70                  75                  80

Ser Glu Asn Ser Leu Gln Phe Phe Leu Pro Val Ile Ala Ser Leu Tyr
                85                  90                  95

Leu Gly Ile Ile Val Ala Pro Val Asn Asp Lys Tyr Ile Glu Arg Glu
            100                 105                 110

Leu Ile His Ser Leu Gly Ile Val Lys Pro Arg Ile Val Phe Cys Ser
            115                 120                 125

Lys Asn Thr Phe Gln Lys Val Leu Asn Val Lys Ser Lys Leu Lys Ser
130                 135                 140

Ile Glu Thr Ile Ile Ile Leu Asp Leu Asn Glu Asp Leu Gly Gly Tyr
145                 150                 155                 160

Gln Cys Leu Asn Asn Phe Ile Ser Gln Asn Ser Asp Ser Asn Leu Asp
                165                 170                 175

Val Lys Lys Phe Lys Pro Tyr Ser Phe Asn Arg Asp Asp Gln Val Ala
                180                 185                 190

Ser Ile Met Phe Ser Ser Gly Thr Thr Gly Leu Pro Lys Gly Val Met
            195                 200                 205

Leu Thr His Lys Asn Ile Val Ala Arg Phe Ser Ile Ala Lys Asp Pro
210                 215                 220

Thr Phe Gly Asn Ala Ile Asn Pro Thr Ser Ala Ile Leu Thr Val Ile
225                 230                 235                 240

Pro Phe His His Gly Phe Gly Met Met Thr Thr Leu Gly Tyr Phe Thr
                245                 250                 255

Cys Gly Phe Arg Val Val Leu Met His Thr Phe Glu Glu Lys Leu Phe

```
                260                 265                 270
Leu Gln Ser Leu Gln Asp Tyr Lys Val Glu Ser Thr Leu Leu Val Pro
            275                 280                 285

Thr Leu Met Ala Phe Leu Ala Lys Ser Ala Leu Val Glu Lys Tyr Asp
        290                 295                 300

Leu Ser His Leu Lys Glu Ile Ala Ser Gly Ala Pro Leu Ser Lys
305                 310                 315                 320

Glu Ile Gly Glu Met Val Lys Lys Arg Phe Lys Leu Asn Phe Val Arg
                325                 330                 335

Gln Gly Tyr Gly Leu Thr Glu Thr Thr Ser Ala Val Leu Ile Thr Pro
            340                 345                 350

Lys Gly Asp Ala Lys Pro Gly Ser Thr Gly Lys Ile Val Pro Leu His
        355                 360                 365

Ala Val Lys Val Val Asp Pro Thr Thr Gly Lys Ile Leu Gly Pro Asn
    370                 375                 380

Glu Pro Gly Glu Leu Tyr Phe Lys Gly Pro Met Ile Met Lys Gly Tyr
385                 390                 395                 400

Tyr Asn Asn Glu Glu Ala Thr Lys Ala Ile Ile Asp Asn Asp Gly Trp
                405                 410                 415

Leu Arg Ser Gly Asp Ile Ala Tyr Tyr Asp Asn Asp Gly His Phe Tyr
            420                 425                 430

Ile Val Asp Arg Leu Lys Ser Leu Ile Lys Tyr Lys Gly Tyr Gln Val
        435                 440                 445

Ala Pro Ala Glu Ile Glu Gly Ile Leu Leu Gln His Pro Tyr Ile Val
    450                 455                 460

Asp Ala Gly Val Thr Gly Ile Pro Asp Glu Ala Ala Gly Glu Leu Pro
465                 470                 475                 480

Ala Ala Gly Val Val Val Gln Thr Gly Lys Tyr Leu Asn Glu Gln Ile
                485                 490                 495

Val Gln Asp Tyr Val Ala Ser Gln Val Ser Thr Ala Lys Trp Leu Arg
            500                 505                 510

Gly Gly Val Lys Phe Leu Asp Glu Ile Pro Lys Gly Ser Thr Gly Lys
        515                 520                 525

Ile Asp Arg Lys Val Leu Arg Gln Met Leu Glu Lys His Thr Asn Gly
    530                 535                 540

<210> SEQ ID NO 3
<211> LENGTH: 5
<212> TYPE: PRT
<213> ORGANISM: Artificial Sequence
<220> FEATURE:
<223> OTHER INFORMATION: Synthetic

<400> SEQUENCE: 3

Val Asp Val Ala Asp
1               5

<210> SEQ ID NO 4
<211> LENGTH: 4
<212> TYPE: PRT
<213> ORGANISM: Artificial Sequence
<220> FEATURE:
<223> OTHER INFORMATION: Synthetic

<400> SEQUENCE: 4

Asp Glu Val Asp
1
```

```
<210> SEQ ID NO 5
<211> LENGTH: 4
<212> TYPE: PRT
<213> ORGANISM: Artificial Sequence
<220> FEATURE:
<223> OTHER INFORMATION: Synthetic

<400> SEQUENCE: 5

Val Glu Ile Asp
1

<210> SEQ ID NO 6
<211> LENGTH: 4
<212> TYPE: PRT
<213> ORGANISM: Artificial Sequence
<220> FEATURE:
<223> OTHER INFORMATION: Synthetic

<400> SEQUENCE: 6

Leu Glu Thr Asp
1

<210> SEQ ID NO 7
<211> LENGTH: 4
<212> TYPE: PRT
<213> ORGANISM: Artificial Sequence
<220> FEATURE:
<223> OTHER INFORMATION: Synthetic

<400> SEQUENCE: 7

Leu Glu His Asp
1
```

REAL-TIME MONITORING

This application is a continuation of U.S. patent application Ser. No. 14/038,438, filed Sep. 26, 2013, which claims priority to U.S. Provisional Patent Application No. 61/705,993 filed Sep. 26, 2012, each of which is herein incorporated by reference in its entirety.

FIELD

Provided herein are methods for the real-time monitoring of an event or response. In particular, the methods provided herein monitor the conversion of a stable pro-substrate to an unstable substrate for a protein sensor, as a result of an event or response.

BACKGROUND

The monitoring of an intracellular, extracellular, or other event or response (e.g., reduction of metabolic activity, changes in intracellular radicals, induction of apoptosis, etc.) in response to various cellular insults brought on by chemical or biochemical compounds is an important aspect for the study of diverse biological events.

SUMMARY

In some embodiments, the methods described herein comprise a noninvasive approach (e.g., bioluminescent assay) for continuous, real-time detection and/or measurement of an event, response, condition, or signal. In general, a stable pro-substrate (or one present in excess or continually added throughout the course of the assay) is continuously converted into substrate in response to an event, agent, condition, etc., and the presence of the substrate is detected by its interaction with a sensor (e.g., protein sensor). The generated substrate is rapidly eliminated due to its inherent instability (or due to its rapid utilization by the protein sensor) resulting in conditions where no significant amount of the substrate is able to accumulate, allowing measurement of the event, response, condition, or signal in real-time or near real-time, i.e., as they occur. Any changes in the activity of a measured event result in the change of substrate production and, subsequently, in the change of the signal generated by the sensor and substrate.

Various embodiments of the invention are useful for detecting/monitoring intracellular and/or extracellular events, responses, conditions, or signals. Detection of events, responses, conditions, or signals in cell lysate or cell-free systems is also within the scope of the present invention. In some embodiments, the ability of the pro-substrate and/or substrate to enter and/or exit cells is tailored for the location (e.g., intracellular, extracellular, cell-free) of the event, response, condition, or signal to be detected. In some embodiments, pro-substrate is converted into substrate intracellularly. In some embodiments, pro-substrate is converted into substrate extracellularly. In some embodiments, pro-substrate is converted into substrate in a cell lysate. In some embodiments, pro-substrate is converted into substrate in a cell-free system. In some embodiments, pro-substrate and/or substrate that are capable of entering and/or exiting cells by any suitable mechanism are used in the detection of intracellular, extracellular, and/or cell-free events, responses, conditions, or signals. In some embodiments, pro-substrate and/or substrate that are not capable of entering and/or exiting cells are used in the detection of extracellular and/or cell-free events, responses, conditions, or signals. Although many of the embodiments described herein are described in the context of cellular events, the compositions and methods are also applicable to cell lysates and/or cell-free systems. Many embodiments described herein are described as applying to the detection of intracellular events; however, unless specifically noted as being for intracellular use only and not for extracellular or cell-free use, these embodiments are also applicable to the monitoring of extracellular and/or cell-free events as well.

An aspect of embodiments of the present invention, and one that is at least partially responsible for the real-time capabilities of assays utilizing this technology, is the continuous conversion of a pro-substrate into a substrate in response to an event (e.g., an intracellular event, an extracellular event), and its continuous elimination due to substrate instability and/or rapid utilization/degradation of the substrate (e.g., relative to the pro-substrate, relative to the assay time-scale, relative to the timescale of the events being monitored, etc.) by a protein sensor (e.g., a protein sensor present outside the cells). In certain embodiments, the substrate is rapidly utilized by the protein sensor. In other embodiments, the substrate is inherently unstable (e.g., chemically unstable, readily enzymatically degraded), and therefore does not accumulate. Rapid utilization, consumption, and/or degradation of the substrate results in little or no extracellular substrate accumulation. Because the substrate does not accumulate and/or is only present for a relatively short time (e.g., relative to the pro-substrate, relative to the assay time-scale, relative to the timescale of the events being monitored, etc.), the signal generated by the substrate and the protein sensor depends on the continuous production of substrate by a cellular event and is directly proportional to the activity of measured intracellular events. In some embodiments, continuous production of substrate inside the cells (or extracellularly) and continuous usage of it by a protein sensor outside the cells provides an assay in which a steady state signal output level is achieved that reflects the magnitude, frequency, and or concentration of the event, response, condition or agent and changes primarily as a function of changes in the levels thereof. In such embodiments, should the rate of conversion of pro-substrate to substrate decrease (e.g., due to slowing of the conversion, due to lack of availability of intracellular pro-substrate), it is reflected in a real-time decrease in signal. Likewise, should the rate of conversion of pro-substrate to substrate increase (e.g., due to faster conversion rate, due to increased availability of intracellular pro-substrate), it is reflected in a real-time increase in signal. In some embodiments, continuous monitoring of signal provides real-time readout of events, conditions, activities, etc.

In some embodiments, the signal generated at any given time is proportional to the event or response that is being monitored. In some embodiments, the generation of signal depends on measuring the activity of an enzyme or molecule that may be attributed to an intracellular event or response in a living cell. In some embodiments, if the event, response or activity to be measured is inhibited or the cells are lysed, no signal (or reduced signal) is generated. In some embodiments, the generation of signal depends on measuring the activity of an enzyme or molecule that may be attributed to an extracellular event or response. In such embodiments, if the event, response or activity to be measured is inhibited or if export of key agents is inhibited, no signal (or reduced signal) is generated.

In some embodiments, a pro-substrate is continuously converted into a substrate by a condition, event, response, or an agent that results therefrom. In some embodiments, a pro-substrate is continuously converted into a substrate intracellularly, extracellularly, in cell lysate, or in a cell-free system. In certain embodiments, the characteristics of the pro-substrate (e.g., concentration, stability, etc.) and/or assay conditions (e.g., amount of pro-substrate added, protein sensor concentration, number of pro-substrate additions, etc.) are selected/manipulated to ensure that sufficient concentration of pro-substrate is present throughout the assay. Sufficient pro-substrate concentration is a concentration that results in interaction of the pro-substrate with an intracellular event, condition, response, or agent associated therewith when such an event, condition, response occurs. In some embodiments, the pro-substrate is stable over the time-scale of the assay (e.g., $T_{1/2}$ assay run time). In some embodiments, pro-substrate concentration is adjusted to compensate for any instability of the pro-substrate (e.g., greater pro-substrate concentration for a less stable pro-substrate). In some embodiments, sufficient pro-substrate is provided to ensure its conversion to the substrate, should the proper intracellular condition, event, response, agent occur or be present. In some embodiments, repeated additions of pro-substrate are made over the course of the assay. In some embodiments, pro-substrate is continuously flowed into the assay.

In some embodiments, the systems and methods provided herein comprise (a) a protein sensor (e.g., a luciferase enzyme) and (b) a pro-substrate (e.g., an entity that can be converted into a substrate for the protein sensor). In embodiments of the present invention, a protein sensor and pro-substrate are introduced extracellularly. The pro-substrate is able to move from the extracellular space into the interior of cells by any suitable mechanism (e.g., diffusion, endocytosis, passive transport, active transport, etc.). In some embodiments, the pro-substrate is also capable of exiting the intracellular environment and returning to the extracellular space (e.g., by any suitable mechanism). Suitable pro-substrates include entities that are converted to substrate inside live cells in response to a cellular event. The substrate moves out of the live cell and is utilized by the protein sensor placed outside the cells to produce a signal that can be measured and represents direct measurement of an intracellular event.

In other embodiments, the extracellularly-introduced pro-substrate is incapable of moving into the interior of cells. In such embodiments, the pro-substrate is converted to substrate outside of cells in response to an event (e.g., extracellular, intracellular, etc.). In some embodiments, pro-substrate is converted to substrate upon cell export of a particular agent. In some embodiments, the rate of conversion is dependent upon the amount of export of an agent. In these embodiments, the pro-substrate is introduced extracellularly, converted to substrate extracellularly, and utilized by the protein sensor extracellularly to produce a signal that can be measured and represents direct measurement of an event or condition (e.g., extracellular, intracellular, etc.).

In yet other embodiments, the protein sensor and the pro-substrate are introduced into a cell lysate or cell-free system. The pro-substrate is converted into substrate upon the occurrence of an event or condition of interest and the substrate is utilized by the protein sensor. In such embodiments, there is no need for the presence of cells.

Some suitable pro-substrates comprise a substrate moiety and a functional moiety (or blocking moiety). In some embodiments, a functional moiety (or blocking moiety) is an entity or functional group (e.g., peptide, organic molecule, etc.) that can be severed from the substrate moiety by an event (e.g., enzymatic cleavage, chemical cleavage, etc.). When the functional moiety is removed from the substrate moiety (e.g., by an intracellular event) the substrate for the protein sensor is liberated.

Other suitable pro-substrates are incomplete substrates (e.g., pro-substrate becomes a substrate upon addition of a moiety or functional group). In certain embodiments, a functional moiety is an entity (e.g., peptide, organic molecule, etc.) that is added to the pro-substrate by an event (e.g., chemical reaction, enzymatically facilitated addition, etc.), to produce a substrate.

In various embodiments, the substrate (e.g., liberated from the blocking moiety, modified by an intracellular event, etc.) is free to interact with the protein sensor (e.g., in the extracellular space, in the intracellular space). Upon exposure of the substrate (e.g., freed from the functional element, modified from its "pro" form, etc.) to the protein sensor, the substrate is utilized by the protein sensor to produce a detectable signal (e.g., luminescence). In some embodiments, the substrate is altered, consumed, and/or degraded by the protein sensor such that it cannot again be utilized by a sensor protein in the signal-producing reaction. The alteration, consumption, and/or degradation of the substrate by the protein sensor results in no accumulation of the substrate.

In some embodiments, the substrate is rapidly degraded (e.g., chemically, enzymatically, etc.), consumed (e.g., by the protein sensor), or otherwise eliminated following its generation by the interaction of the pro-substrate with the agent associated with the response, event, or condition of interest. The instability of the substrate can result from one or a combination of: the inherent instability of the substrate, susceptibility of the substrate to degradation or modification, utilization of the substrate by the protein sensor, instability of the substrate under physiological and/or intracellular conditions, etc. As a result, little to no (e.g., substantially none) substrate accumulates (e.g., intracellularly, extracellularly, etc.) during the course of an assay.

In some embodiments, a protein sensor is an enzyme. In some embodiments, a protein sensor produces a detectable signal upon interaction with a substrate. The protein sensor is present in an amount required for rapid substrate utilization. A protein sensor retains activity outside the cell over the time-scale of the assay. In some embodiments, a protein sensor is a luciferase, chromophoric protein, fluorescent protein, etc. In some embodiments, the protein sensor is a luciferase selected from those found in *Omphalotus olearius*, fireflies (e.g., Photinini), *Renilla reniformis*, mutants thereof, portions thereof, variants thereof, and any other luciferase enzymes suitable for the systems and methods described herein. In some embodiments, the protein sensor is a modified, enhanced luciferase enzyme from *Oplophorus* (e.g., NANOLUC luciferase enzyme from Promega Corporation, SEQ ID NO: 1 or a sequence with at least 70% identity (e.g., >70%, >80%, >90%, >95%) thereto). In some embodiments, the protein sensor is a thermostable *Photuris pennsylvanica* luciferase (e.g., SEQ ID NO: 2 or a sequence with at least 70% identity (e.g., >70%, >80%, >90%, >95%) thereto).

In some embodiments, a pro-substrate is provided, introduced, and/or administered to a sample and/or the extracellular space. In some embodiments, a pro-substrate is converted to a substrate for a protein sensor by an enzyme of interest, target enzyme, or other agent. In some embodiments, a pro-substrate comprises a substrate moiety (e.g., substrate for the protein sensor) and an additional moiety (e.g., functional moiety, blocking moiety, etc.), wherein the additional moiety is removed from the pro-substrate (e.g., by an enzyme of interest) to produce a substrate for the protein sensor. In some embodiments, a pro-substrate lacks a functional group or chemical moiety of a whole substrate and addition of that group or moiety to the pro-substrate converts the pro-substrate into a substrate. In some embodiments, chemical and/or enzymatic modification of the pro-substrate results in the formation of the substrate. In some embodiments, the pro-substrate structure is converted into a substrate structure (e.g., chemically, enzymatically, etc.). In some embodiments, the substrate is a substrate for a luciferase enzyme. In some embodiments, the pro-substrate is a pro-substrate for a luciferase enzyme. In some embodiments, the pro-substrate is a pro-substrate for a modified, enhanced luciferase enzyme from *Oplophorus*, e.g., NANOLUC luciferase enzyme from Promega Corporation (e.g., SEQ ID NO: 1). In some embodiments, the pro-substrate comprises coelenterazine, a coelenterazine derivative, a structural or functional equivalent of coelenterazine, a molecule substantially equivalent to coelenterazine (e.g., structurally and/or functionally), or molecule functionally or structurally similar to coelenterazine. In some embodiments, the pro-substrate comprises Formula I:

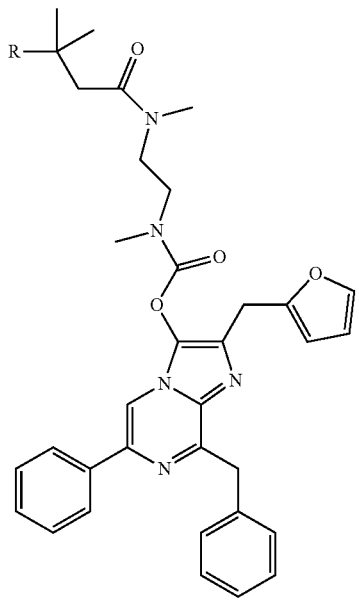

wherein R comprises an organic moiety, peptide, amino acid, nucleotide, or nucleic acid that can be acted upon, e.g., removed or modified, by an enzyme of interest. The above is an exemplary pro-substrate that provides a model for other pro-substrates for other coelenterazine-utilizing luciferases, other luciferase, or other enzymes.

In some embodiments, upon being acted on by the enzyme of interest or other agent (e.g., intracellularly, extracellular, in a cell-free environment, etc.), the pro-substrate is converted to a substrate for the protein sensor. In some embodiments, the substrate diffuses from the cell into the extracellular space (e.g., media, etc.). In some embodiments, the pro-substrate is added to living cells. In some embodiments, the pro-substrate and the protein sensor are added simultaneously. In some embodiments, the pro-substrate and the protein sensor are added at different times. In some embodiments, the pro-substrate is stable for an extended period of time (e.g., >1 hour, >2 hours, >6 hours, >12 hours, >24 hours, >48 hours, >72 hours, >100 hours). In some embodiments, the protein sensor is stable for an extended period of time (e.g., >1 hour, >2 hours, >6 hours, >12 hours, >24 hours, >48 hours, >72 hours, >100 hours).

In some embodiments, the method disclosed herein can be used for studying diverse biological events, including but not limited to: metabolic activity of live cells, apoptosis by measuring caspase activation, generation of reactive oxygen species by measuring hydrogen peroxide formation, reducing capacity of the cell, oxidative capacity of the cell, etc. In some embodiments, a biological event or intracellular event, response, or condition (e.g., reducing capacity, oxidative capacity, etc.) may be attributed to a particular enzyme or molecule, e.g., protein. In some embodiments, the enzyme comprises a caspase, a protease, a cytochrome P450 (CYP450) enzyme, or monoamine oxidase (MAO), reductase, dehydrogenase, oxidoreductase, enzymes involved in oxidative phosphorylation, enzymes involved in glycolysis, etc. In some embodiments, the method described herein allows for the detection, measurement, e.g., quantitation, of the enzyme or molecule, e.g., protein or reactive oxygen species.

Embodiments of the present invention find use in any suitable living cells, including but not limited to bacterial cells (e.g., *E. coli*), eukaryotic cells (e.g., *X. laevis, C. elegans, S. cerevisiae*), and mammalian cells (e.g., non-human primates, chicken, mouse, human, etc.). In some embodiments, cells used in embodiments described herein are in cultured cells, in vitro, in situ, or in vivo. In some embodiments, pro-substrate conversion to substrate and substrate utilization by the protein sensor both take place outside of cells (e.g., extracellularly) or in an environment lacking living cells (e.g., cell lysate, cell-free system, etc.).

In some embodiments, the substrate is unstable (e.g., inherently unstable, rapidly degraded by the sensor protein). In some embodiments, the instability of the substrate allows for the real-time monitoring of an event or response (e.g., intracellular event or response). The instability of the substrate prevents substrate accumulation such that a steady state signal output level is achieved that reflects the presence of the agent of interest and changes primarily as a function of changes in the concentration of activity of the agent of interest. The instability of the substrate may be derived from the chemical instability of the substrate and/or the rapid consumption of the substrate by a protein sensor. Because of the instability of the substrate, the signal generated by a protein sensor necessarily results from a recently converted substrate (e.g., converted from pro-substrate). In some embodiments, the pro-substrate is stable. In some embodiments, processing of the pro-substrate (e.g., by live cells) creates an unstable active substrate for the protein sensor. In some embodiments, an intracellular event or response (e.g., directly or indirectly resulting in conversion of the pro-substrate into the substrate) can be monitored over an extended period of time due to the stability of both the pro-substrate and the protein sensor (e.g., stability of the pro-substrate inside and/or outside the cell and/or stability of the protein sensor outside the cell).

In some embodiments, the method described herein does not require engineering of a living cell (e.g., the protein sensor does not need to be expressed by the living cell). In some embodiments, the protein sensor does not enter the cell. In some embodiments, the method described herein can be used with different pro-substrates, e.g., pro-furimazine, pro-coelenterazine, pro-coelenterazine derivative or analog, or pro-luciferin, and different protein sensors, e.g., different luciferase enzymes, e.g., luciferase enzymes from *Oplophorus, Photinus pyralis, Photuris pennsylvanica, Renilla*, or *Gaussia*. In some embodiments, the luciferase enzyme may be modified, e.g., have enhanced bioluminescence, enhanced signal stability, or is thermostable. In some embodiments, the method described herein can be used in different biological systems, e.g., bacteria, yeast, eukaryotic, e.g., mammalian, cells, tissues, and animal models. In some embodiments, the methods described herein can be used to monitor, in real-time, an intracellular event or response in vivo, e.g., inside a cell(s), tissue or organ of a living animal, e.g., mouse, rat, or human.

In some embodiments, the present invention provides methods of detecting an intracellular event, condition, or response comprising: (a) providing: (i) a cell; (ii) a protein sensor, wherein the protein sensor generates a detectable signal upon interaction with a substrate, and (iii) a stable pro-substrate, wherein the pro-substrate is capable of entering the cell, wherein interaction of the pro-substrate with an agent associated with the intracellular event, condition, or response converts the pro-substrate into the unstable substrate for the protein sensor; (b) detecting the signal generated by the interaction of the substrate and the protein sensor, wherein the presence of the signal indicates the occurrence of the intracellular event, condition, or response in real time, wherein the absence of an agent associated with the intracellular event, condition, or response results in the real-time absence of the signal, and wherein the magnitude of the signal correlates with the amount of the agent.

In some embodiments, the present invention provides methods of detecting an event, condition, or response comprising: (a) providing: (i) a cell; (ii) a protein sensor, wherein the protein sensor generates a detectable signal upon interaction with a substrate, and (iii) a stable pro-substrate, wherein the pro-substrate is incapable of entering the cell, wherein interaction of the pro-substrate with an agent associated with the event, condition, or response converts the pro-substrate into the unstable substrate for the protein sensor; (b) detecting the signal generated by the interaction of the substrate and the protein sensor, wherein the presence of the signal indicates the occurrence of the event, condition, or response in real time, wherein the absence of an agent associated with the extracellular event, condition, or response results in the real-time absence of the signal, and wherein the magnitude of the signal correlates with the amount of the agent. In some embodiments, the event, condition, or response is extracellular or intracellular.

In some embodiments, the present invention provides methods of extracellularly detecting an event, condition, or response comprising: (a) providing: (i) a cell; (ii) a protein sensor, wherein the protein sensor generates a detectable signal upon interaction with a substrate, and (iii) a stable pro-substrate, wherein the pro-substrate is incapable of entering the cell, wherein interaction of the pro-substrate with an agent associated with the event, condition, or response converts the pro-substrate into the unstable substrate for the protein sensor; (b) detecting the signal generated by the interaction of the substrate and the protein sensor, wherein the presence of the signal indicates the occurrence of the event, condition, or response in real time, wherein the absence of an agent associated with the extracellular event, condition, or response results in the real-time absence of the signal, and wherein the magnitude of the signal correlates with the amount of the agent. In some embodiments, the present invention provides methods of extracellularly detecting an event, condition, or response comprising: (a) providing: (i) a cell; (ii) a protein sensor, wherein the protein sensor generates a detectable signal upon interaction with a substrate, and (iii) a stable pro-substrate, wherein the pro-substrate is not converted to substrate intracellularly, wherein interaction of the pro-substrate with an agent associated with the event, condition, or response converts the pro-substrate into the unstable substrate for the protein sensor; (b) detecting the signal generated by the interaction of the substrate and the protein sensor, wherein the presence of the signal indicates the occurrence of the event, condition, or response in real time, wherein the absence of an agent associated with the extracellular event, condition, or response results in the real-time absence of the signal, and wherein the magnitude of the signal correlates with the amount of the agent.

In some embodiments, the present invention provides methods of detecting an event, condition, or response comprising: (a) providing: (i) a cell lysate or cell-free media; (ii) a protein sensor, wherein the protein sensor generates a detectable signal upon interaction with a substrate, and (iii) a stable pro-substrate, wherein interaction of the pro-substrate with an agent associated with the event, condition, or response converts the pro-substrate into the unstable substrate for the protein sensor; (b) detecting the signal generated by the interaction of the substrate and the protein sensor, wherein the presence of the signal indicates the occurrence of the event, condition, or response in real time, wherein the absence of an agent associated with the extracellular event, condition, or response results in the real-time absence of the signal, and wherein the magnitude of the signal correlates with the amount of the agent.

In some embodiments, detecting comprises real-time monitoring. In some embodiments, the substrate is unstable. In some embodiments, the substrate does not accumulate (e.g., extracellularly) following the interaction of the pro-substrate with the agent associated with the event, condition, or response. In some embodiments, substantially all of the substrate generated by interaction of the pro-substrate with the agent associated with the event, condition, or response is either degraded or utilized by the protein sensor.

In some embodiments, substantially all (e.g., all detectable amounts under assay detection conditions) of the substrate generated by interaction of the pro-substrate with the agent associated with the event, condition, or response (e.g., intracellular event, condition, or response) is either degraded or utilized by the protein sensor within a time-frame that is useful for real-time or near real-time detection of the interaction (e.g., depending upon the type of assay, the length of the experiment, and the event or condition being monitored, substrate may be degraded or utilized within 1 second, 2 seconds, 5 seconds, 10 seconds, 20 seconds, 1 minute, 2 minutes, 5 minutes, 10 minutes, 20 minutes, or more time following substrate generation). In some embodiments, substantially all of the substrate generated by interaction of the pro-substrate with the agent associated with the intracellular event, condition, or response is either degraded or utilized by the protein sensor within 1 minute of the interaction. In some embodiments, substantially all of the substrate generated by interaction of the pro-substrate with the agent associated with the intracellular event, condition, or response is either degraded or utilized by the protein sensor within 30 seconds of the interaction. In some embodiments, substantially all of the substrate generated by interaction of the pro-substrate with the agent associated with the intracellular event, condition, or response is either degraded or utilized by the protein sensor within 10 seconds of the interaction. In some embodiments, the substrate is a real-time substrate.

In some embodiments, the signal generated by the interaction of the substrate and the protein sensor only persists when substrate is continually produced by interaction of the pro-substrate with the agent associated with the intracellular event, condition, or response. In some embodiments, increases and decreases in the concentration of the agent associated with the intracellular event, condition, or response result in corresponding increases and decreases in the signal generated by the interaction of the substrate and the protein sensor. In some embodiments, changes in the signal occur within 5 minutes of changes in agent concentration. In some embodiments, changes in the signal occur within 1 minute of changes in agent concentration. In some embodiments, changes in the signal occur within 30 seconds of changes in agent concentration. In some embodiments, changes in the signal occur within 10 seconds of changes in agent concentration. In some embodiments, the signal is a real-time signal. In some embodiments, the signal is a non-accumulated signal.

In certain embodiments, the pro-substrate enters cells at a certain rate (e.g., constant or varied by an operator or experimenter over the course of an assay). In certain embodiments, the pro-substrate is converted into substrate at a certain rate (e.g., constant or varied over the course of an assay). In some embodiments, the rate of pro-substrate entry is sufficient to provide a pool of intracellular pro-substrate for conversion into substrate at whatever rate the cell is capable of. In some embodiments, pro-substrate entry into cells is not rate limiting to the production of signal from substrate. In some embodiments, substrate exit from the cell is not rate limiting to the production of signal. In some embodiments, conversion of pro-substrate to substrate is rate limiting to the production of signal. In some embodiments, the conversion of pro-substrate to substrate acts as the 'gatekeeper' (or limiting factor), determining the amount of substrate that is made available for detection. In such embodiments, conversion from pro-substrate to substrate is regulated by cellular conditions, activities and/or events. When events, conditions, or activities raise the rate of conversion, the amount of substrate, and therefore the amount of signal produced increases. When events, conditions or activities slow the rate of conversion (or stop conversion), the amount of substrate, and therefore the amount of signal produced decreases. In such embodiments, the rate of conversion of pro-substrate to substrate and not the rate of pro-substrate entry or substrate exit is controlling (e.g., allowing the monitoring of events/conditions that affect the rate of pro-substrate conversion). The substrate does not accumulate intracellularly, for example, because the substrate is degraded or utilized before any such accumulation can occur. If the cell fails to convert pro-substrate into substrate or slows its conversion (e.g., due to cellular conditions or events), the signal detected decreases. When cells more rapidly convert pro-substrate to substrate (e.g., due to cellular conditions or events), the signal detected increases. In technologies where substrate accumulates, even if conversion of pro-substrate ceases, the signal persists. In embodiments of the present invention, increases or decreases in signal are directly attributable to corresponding increases or decreases in the amount of substrate produced and the cellular activity or agent responsible for the conversion of the pro-substrate.

In certain embodiments, methods provided herein allow for the pinpointing of maximal effect, minimal effect, and/or transition points of the studied event, response, or condition. Among other advantages of such an assay, assays with such functionality allow experimenters to design functional end point assays which occur at the most optimal time.

In some embodiments, the protein sensor is provided extracellularly. In some embodiments, the protein sensor is incapable of entering the cell. In some embodiments, the interaction of the substrate and the protein sensor occurs extracellularly.

In some embodiments, the protein sensor comprises a luciferase enzyme. In some embodiments, the luciferase enzyme comprises an *Oplophorus*, beetle, *Renilla* or *Gaussia* luciferase. In some embodiments, the luciferase enzyme comprises a luciferase with enhanced protein stability enhanced bioluminescence and/or enhanced signal stability. In some embodiments, the luciferase enzyme comprises an *Oplophorus* luciferase with enhanced protein stability enhanced bioluminescence and/or enhanced signal stability. In some embodiments, the luciferase enzyme comprises a beetle luciferase selected from *Photinus pyralis* or *Photuris pennsylvanica*. In some embodiments, the pro-substrate comprises a pro-furimazine, pro-furimazine derivative, pro-coelenterazine, pro-coelenterazine derivative or analog, pro-luciferin, or pro-luciferin derivative.

In some embodiments, the agent (e.g., agent responsible for the conversion of pro-substrate to substrate) is an enzyme or molecule, the presence of which correlates to the intracellular event or response. In some embodiments, the enzyme or molecule comprises a caspase, a protease, a reactive oxygen species, a cytochrome P450 (CYP450) enzyme, or monoamine oxidase (MAO), reductase, dehydrogenase, or oxidoreductase.

In some embodiments, the present invention provides kits for detecting an intracellular event or response, the kit comprising: (a) a protein sensor, wherein the protein sensor generates a detectable signal upon interaction with a substrate, and (b) a pro-substrate, wherein the pro-substrate is capable of entering a cell, wherein interaction of the pro-substrate with an agent associated with the intracellular event, condition, or response converts the pro-substrate into a substrate for the protein sensor. Any of the compositions useful in carrying out embodiments of the present invention (e.g., protein sensor, pro-substrates, buffers, cells, controls, etc.), alone or in combination with other compositions, may be provided in the form of a kit. For example, protein sensor and pro-substrate may be provided in a kit for detection of a cellular condition (e.g., cell viability). Kits may further comprise appropriate controls (e.g., negative, positive), containers, assay reagents, and/or detection reagents.

In certain embodiments, the signal is detected by any suitable device, detector, apparatus, system, etc. Depending upon the detectable signal (e.g., luminescence, colorimetric, etc.), and/or the assay conditions (e.g., multiplex, cell type, etc.), suitable detectors may include, but are not limited to: CCD cameras, video cameras, photographic film, laser scanning devices, fluorometers, photodiodes, quantum counters, epifluorescence microscopes, scanning microscopes, flow cytometers, fluorescence microplate readers, or a fluorescence microscope. In some embodiments, detection is by real-time monitoring, end-point reads, sequential, continuous reads (e.g., every: 1 second, 2 seconds, 5 seconds, 10 seconds, 30 seconds, 1 minute, 2 minutes, etc.), or any other suitable detection/monitoring scheme.

In some embodiments, a computer-based analysis program is used to correlate the raw data generated by the detection assay (e.g., the presence, absence, or amount of signal) into the concentration of an agent of interest or the magnitude, frequency and/or concentration of an event, condition, and or response related to that agent. The data may be reported in any suitable format (e.g., raw signal data, converted signal, agent concentration, event frequency, cellular conditions, etc.). The data may be stored (e.g., in a computer-readable format), displayed (e.g., on a monitor), printed, reported, etc. In some embodiments, methods provide computer-assisted analysis of the data (e.g., raw or correlated).

In some embodiments, the present invention provides methods of detecting an event, condition, or response comprising: detecting a signal generated by the interaction of a substrate and a protein sensor; wherein the substrate is the product of an interaction of the pro-substrate with an agent associated with the event, condition, or response; wherein the presence of the signal indicates the occurrence of the event, condition, or response in real time; wherein the absence of an agent associated with the event, condition, or response results in the real-time absence of the signal; and wherein the magnitude of the signal correlates with the amount of the agent. In some embodiments, the event, condition, or response is intracellular, extracellular, or cell-free. In some embodiments, detecting comprises real-time monitoring. In some embodiments, detecting comprises endpoint detection. In some embodiments, detecting comprises continuous monitoring of the signal. In some embodiments, detecting comprises continuous monitoring of intracellular events in live cells over extended period of time (e.g., 10 minutes . . . 20 minutes . . . 1 hour . . . 2 hours . . . 4 hours . . . 12 hours . . . 24 hours . . . 48 hours . . . 72 hours, 1 week, 4 weeks, or more). In some embodiments, the pro-substrate is stable and continuously enters the cell. In some embodiments, the pro-substrate is converted to a substrate by an intracellular event, condition or response and continuously exits the cell. In some embodiments, the substrate generates a signal by interaction with a protein sensor placed outside the cell. In some embodiments, the substrate is unstable (e.g., degraded and or utilized in <30 seconds, <1 minute, <2 minutes, <5 minutes, <10 minutes, <30 minutes, <1 hours, or any other timescale that is rapid with respect to the timescale of the experiment or assay). In some embodiments, the substrate does not accumulate (e.g., extracellularly) following the interaction of the pro-substrate with the agent associated with the intracellular event, condition, or response. In some embodiments, substantially all of the substrate generated by interaction of the pro-substrate with the agent associated with the intracellular event, condition, or response is either degraded or utilized by the protein sensor. In some embodiments, the signal produced by the substrate and protein sensor depends on a continuous supply of substrate by a live cell. In some embodiments, the substrate is a real-time substrate. In some embodiments, the signal generated by the interaction of the substrate and the protein sensor only persists when substrate is continually produced by interaction of the pro-substrate with the agent associated with the intracellular event, condition, or response. In some embodiments, increases and decreases in the concentration of the agent associated with the intracellular event, condition, or response result in corresponding increases and decreases in the signal generated by the interaction of the substrate and the protein sensor. In some embodiments, the signal is a real-time signal. In some embodiments, the signal is a non-accumulated signal. In some embodiments, the substrate is capable of exiting the cell. In some embodiments, the protein sensor is provided extracellularly. In some embodiments, the protein sensor is incapable of entering the cell. In some embodiments, the interaction of the substrate and the protein sensor occurs extracellularly. In some embodiments, the live cells are not engineered to express the protein sensor. In some embodiments, the pro-substrate, substrate or protein sensor are non-invasive and do not interfere with cellular function. In some embodiments, the protein sensor retains activity over the time scale of the assay. In some embodiments, the protein sensor comprises a luciferase enzyme. In some embodiments, the luciferase enzyme comprises an *Oplophorus*, beetle, *Renilla* or *Gaussia* luciferase. In some embodiments, the luciferase enzyme comprises an *Oplophorus* luciferase with enhanced protein stability, enhanced bioluminescence, and/or enhanced signal stability. In some embodiments, the luciferase enzyme comprises a beetle luciferase selected from *Photinus pyralis* or *Photuris pennsylvanica*. In some embodiments, the pro-substrate comprises a pro-furimazine, pro-furamizine derivative, pro-coelenterazine, pro-coelenterazine derivative or analog, pro-luciferin, or pro-luciferin derivative. In some embodiments, the agent is an enzyme or molecule, the presence of which correlates to the intracellular event or response. In some embodiments, the enzyme or molecule comprises a caspase, a protease, a reactive oxygen species, a cytochrome P450 (CYP450) enzyme, or monoamine oxidase (MAO), reductase, dehydrogenase, or oxidoreductase. In some embodiments, intracellular event, condition, or response is detected in bacterial cells. In some embodiments, the intracellular event, condition, or response is detected in eukaryotic cells (e.g., mammals, fish, birds, worms insects yeast, etc.). In some embodiments, the intracellular event, condition, or response is detected in mammalian cells (e.g., human, non-human primate, feline, canine, bovine, equine, prcine, rodent, etc.). In some embodiments, the intracellular event, condition, or response occurs is detected in a tissue or whole organism. In some embodiments, multiple different intracellular events, conditions, or responses are detected simultaneously in a multiplex assay or format.

DEFINITIONS

Figure 1:
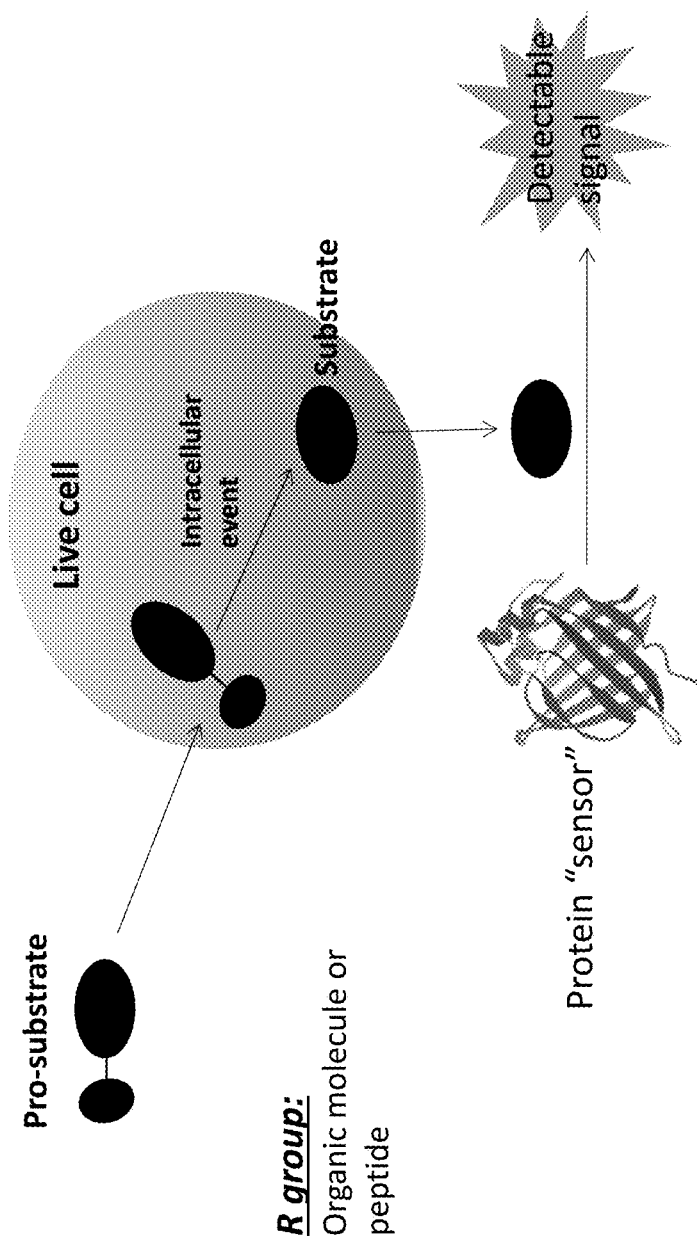
FIG. 1 illustrates the scheme of an assay for the real-time noninvasive continuous monitoring of intracellular events using embodiments of the methods described herein.

As used herein, the term "enzyme or molecule of interest" refers to an enzyme or molecule, e.g., protein, whose activity may be attributed to an event or response.

As used herein, the term "agent" refers to an enzyme or molecule whose presence correlates to a condition, event or response.

As used herein, the term "pro-substrate" refers to a molecule that can be converted by an enzyme or molecule of interest to a substrate for a protein sensor. As used herein, the term "pro-furimazine substrate" refers to a pro-substrate that can be converted to furimazine (e.g., incomplete furimazine, modified furimazine, complete furimazine, etc.). As used herein, the term "pro-coelenterazine" refers to a pro-substrate that can be converted to coelenterazine (e.g., incomplete coelenterazine, modified coelenterazine, complete coelenterazine, etc.). As used herein, the term "pro-luciferin" refers to a pro-substrate that can be converted to luciferin (e.g., incomplete luciferin, modified luciferin, complete luciferin, etc.).

As used herein, the term "converted substrate" refers to a molecule that is a substrate for a protein sensor and was derived from a pro-substrate.

As used herein, the term "protein sensor" refers to an enzyme or protein that utilizes a substrate acted upon by an enzyme or molecule of interest to generate a detectable and/or measureable signal.

As used herein, the term "real-time" refers to an assay in which the timing of a detectable signal is correlated to the timing of an event, response, condition or agent of interest at multiple time points. The signal is detected and/or measured either substantially concurrently with the presence and/or occurrence of the event, response, condition, or agent of interest or after a short lag time. A lag or delay between the timing of an event, response, condition, or agent of interest and the detectable signal is, for example, the result of the time required for the cellular and/or assay steps necessary for detection. Preferably such lag or delay is less than 30 minutes, e.g., 25 minutes, 20 minutes, 15 minutes, 10 minutes, 5 minutes, 4 minutes, 3 minutes, 2 minutes, 1 minute or less, including no lag or delay, or any time period that is short (e.g., <10%, <5%, <2%, <1%) of the time period being monitored. Due to consistent lag times over the time course of an assay, the delayed signal is still suitable to provide real-time readout of the timing of an event, response, condition or agent of interest.

As used herein, the term "real-time substrate" refers to a substrate that is sufficiently unstable and/or accumulated in low enough concentration that substantially all of the signal detected from the interaction of the substrate with a corresponding protein sensor (e.g., >90%, >91%, >95%, >98%, >99%, >99.9%) is the result of substrate generated or added to the system in real-time (e.g., within the preceding 10 minutes, within the preceding 5 minutes, within the preceding 1 minute, within the preceding 30 seconds, within the preceding 10 seconds, within the preceding 5 seconds, within the preceding 1 second, or within a time that is <1% of total experiment/assay time) and not from substrate accumulated from earlier addition or generation.

As used herein, the term "real-time signal" refers to a detectable signal (e.g., light emission) that is directly proportional to or correlated to an event, condition, response, or agent, such that increases in the frequency, magnitude, or concentration of the event, condition, response, or agent result in detectable changes (e.g., increase or decrease) in signal in real-time (e.g., within 10 minutes, within 5 minutes, within 1 minute, within 30 seconds, within 10 seconds, within 5 seconds, within 1 second, or within a time that is <1% of total experiment/assay time), and decreases in the frequency, magnitude, or concentration of the event, condition, response, or agent result in detectable changes (e.g., increase or decrease) in signal in real-time (e.g., within 1 hour, within 30 minutes, within 20 minutes, within 10 minutes, within 5 minutes, within 1 minute, within 30 seconds, within 10 seconds, within 5 seconds, within 1 second).

As used herein, the term "accumulated signal" refers to a detectable signal that, at any given point in time, correlates in magnitude to the sum of the frequencies, magnitudes, or concentrations of events, conditions, responses, or agents over a span of time (e.g., the time course of the assay). The accumulated signal increases at a rate substantially proportional to the frequency, magnitude, or concentration of an event, condition, response or agent. In the absence of an event, condition, response, or agent, the accumulated signal remains substantially constant.

As used herein, the term "non-accumulated signal" refers to a detectable signal that, at any given point in time, correlates in magnitude to the frequency, magnitude, or concentration of an event, condition, response or agent at a given point in time. The non-accumulated signal increases and decreases as the frequency, magnitude, or concentration of an event, condition, response, or agent increases and decreases. Due to the time required for a signal to be generated following the presence or occurrence of the event, condition, response or agent, there may be a lag time between the signal and the event, condition, response, or agent to which it correlates. Depending upon the assay conditions, lag times may be about 10 minutes, about 5 minutes, about 1 minute, about 30 seconds, about 10 seconds, about 5 seconds, about 1 second, less than 1 second, times therein, or a time that is <1% of total experiment/assay time. Consistent lag times over the course of an assay allow real-time, continuous monitoring of the frequency, magnitude, or concentration of an event, condition, response, or agent over a span of time using an assay that reports a non-accumulated signal.

By the term "substantially" it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide.

As used herein, term "luciferin" refers to a molecule of Formula II:

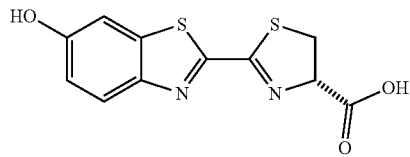 [SMILES: O=C(O)[C@H]1CSC(c2nc3ccc(O)cc3s2)=N1]

Entities such as "modified luciferin," "pro-luciferin," "a luciferin moiety," etc. are variants of the above structure.

As used herein, term "coelenterazine" refers to a molecule of Formula III:

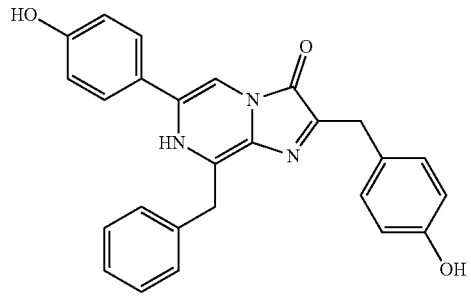 [SMILES: O=c1c(Cc2ccc(O)cc2)nc2c(Cc3ccccc3)[nH]c(-c3ccc(O)cc3)cn1-2]

Entities such as "modified coelenterazine," "pro-coelenterazine," "a coelenterazine moiety," etc. are variants of the above structure.

As used herein, the term "furimazine" refers to a molecule of Formula IV:

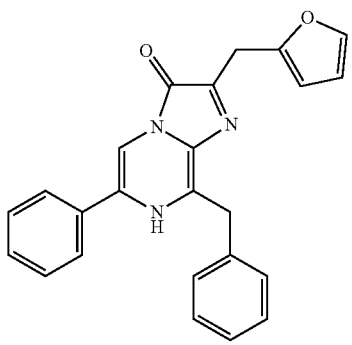 [SMILES: O=c1c(Cc2ccco2)nc2c(Cc3ccccc3)[nH]c(-c3ccccc3)cn1-2]

Entities such as "modified furimazine," "pro-furimazine," "a furimazine moiety," etc. are variants of the above structure.

DETAILED DESCRIPTION

In some embodiments, the systems and methods described herein provide assays (e.g., a bioluminescent assay) for the monitoring and/or measurement of events, conditions, responses, agent concentrations, or signals (e.g., in real time, over an extended time course, etc.). In some embodiments, the systems and methods described herein generate a bioluminescent signal (e.g., from the interaction of a substrate and protein sensor) in real-time response to an event (e.g., that results in conversion of a pro-substrate into a substrate).

In certain embodiments, the systems and methods provided herein comprise a protein sensor and a pro-substrate. In some embodiments, the methods do not require cellular engineering (e.g., alteration of the genetic material of the cell or introduction of genetic material into cell). In some embodiments, the pro-substrate is capable of traversing the cell membrane (e.g., entering a cell, exiting a cell) by any suitable mechanism (e.g., endocytosis, diffusion, passive transport, active transport, etc.). In some embodiments, one or more processes (e.g., chemical, enzymatic, etc.) convert the pro-substrate (e.g., intracellularly) into a substrate for the protein sensor. In some embodiments, the pro-substrate is converted into the substrate within a cell. In some embodiments, the substrate is capable of traversing the cell membrane (e.g., entering a cell, exiting a cell) by any suitable mechanism (e.g., endocytosis, diffusion, passive transport, active transport, etc.). In some embodiments, interaction of the substrate and protein sensor results in a detectable signal (e.g., bioluminescence).

An aspect of many embodiments described herein comprises a system for the continuous flow of pro-substrate into cells; its conversion to a substrate in response to an intracellular event; its release from the cell; and signal generation by the interaction of the substrate with a protein sensor. At any given time, the signal reflects the activity of an intracellular event as it occurs in the cell. The system performs under conditions where the substrate is not accumulated (e.g., to a substantially detectable degree) extracellularly, thereby allowing for real-time measurements, and/or continuous measurements, and/or correlating the detectable signal to the timing of cellular events. Following conversion of the pro-substrate into the substrate by the cellular event, response, condition or agent, the substrate is either completely (e.g., substantially completely) utilized by the protein sensor or otherwise modified or degraded so as to become unusable for later production of a detectable signal.

Because the substrate does not accumulate, any signal detected from a protein sensor is necessarily the result of substrate that was recently converted from the pro-substrate (e.g., within the preceding: 10 minutes, 5 minutes, 2 minutes, 1 minute, 30 seconds, 10 seconds, 5 seconds, 2 seconds, 1 second, or less). In other assays in which the substrate accumulates to a significant degree, signal may be generated from the substrate at any reasonable time over the course of the assay, thereby precluding real-time measurements and/or correlating the detectable signal to the timing of cellular events.

In certain embodiments, the lag time between the event, condition, response or agent of interest and the detectable signal correlatable to its magnitude, frequency, concentration, etc. is the result of the processes required to bring the substrate into contact with the protein sensor (e.g., diffusion, transport across the cell membrane, etc.). When the relevant cellular and/or assay conditions are maintained substantially constant, constant lag times over the course of the assay allow the timing between changes in the detectable signal or particular signal events to be directly correlated to the timing between changes or events in the condition, response, event or agent of interest.

Various mechanisms are employed and/or exploited to ensure the non-accumulation of substrate in the assays described herein. For example, all the substrate may be rapidly consumed by the protein sensor (e.g., protein sensor may be present in excess). The substrate may be inherently unstable, unstable under cellular conditions (e.g., susceptible to protein degradation), or unstable under the assay conditions employed. Substrate may also be produced in very small concentrations (e.g., in comparison to the protein sensor concentration) to ensure that all the substrate is utilized. In certain embodiments, a combination of the above strategies, as well as others, are utilized to ensure that substrate does not accumulate (e.g., intracellularly, extracellularly), thereby allowing real-time monitoring with the assay.

In some embodiments, the method comprises contacting a living cell with a protein sensor comprising an *Oplophorus* luciferase enzyme (e.g., NANOLUC luciferase), and a pro-substrate of the protein sensor that can enter the cell (e.g., pro-furimazine or a pro-furimazine derivative). In an exemplary embodiment, the protein sensor comprises the NANOLUC luciferase enzyme and the pro-substrate comprises a pro-furimazine substrate (e.g., Formula I) comprising an R group, wherein R is selected from: an organic molecule, peptide, nucleic acid, etc. The R group is removed or modified by an enzyme, molecule or agent that may be attributed to an intracellular agent, event, or response, thereby creating a substrate for the protein sensor. Other suitable pro-substrates for an *Oplophorus* luciferase enzyme (or modified version thereof) may comprise incomplete furimazine (e.g., missing a chemical group or moiety) which becomes the furimazine substrate upon addition of the missing element by a cellular event, agent, condition, etc. In certain embodiments, irrespective of the identity of the pro-substrate, once converted into the substrate (e.g., furimazine or a pro-furimazine derivative), the substrate exits (e.g., diffuses from) the cell and is utilized by the protein sensor to generate a signal (e.g., bioluminescence). Using this method, cellular responses are measured in real-time over an extended period of time.

In some embodiments, the method comprises contacting a living cell with a protein sensor comprising a firefly luciferase enzyme (e.g., a luciferase enzyme from *Photinus pyralis* or *Photuris pennsylvanica*), and a pro-luciferin (or pro-[luciferin derivative]) substrate. Due to the relatively high stability of D-luciferin and the slow rate of consumption of luciferin by the firefly luciferase, in some embodiments, accumulation of substrate is prevented by providing a limiting amount of pro-substrate (similar limits on pro-substrate concentration may be utilized in combinations with other techniques with other substrate/sensor pairs) and/or by providing an excess of firefly luciferase enzyme required for rapid substrate utilization. In other embodiments, a more quickly utilized substrate (or sensor that utilizes the substrate more rapidly) or less stable substrate (e.g., a luciferin derivative) is utilized. In some embodiments, an agent is added or conditions are manipulated to prevent luciferin from accumulating. In some embodiments, the pro-luciferin substrate comprises a luciferin moiety and a blocking moiety that prevents the protein sensor from utilizing luciferin as a substrate. In such embodiments, removal or alteration of the blocking group results in a substrate (e.g., luciferin or modified luciferin) that is utilized by the protein sensor to produce a signal. In other embodiments, the pro-luciferin substrate comprises a modified luciferin. In such embodiments, alteration of the modified luciferin results in a substrate (e.g., luciferin or an active modified luciferin) that is utilized by the protein sensor to produce a signal. In some embodiments, a pro-substrate comprises an R group (e.g., organic moiety, peptide, nucleic acid, etc.) that prevents the pro-substrate from being utilized by the protein sensor to produce a signal. In some embodiments, the R group comprises both blocking functionality (e.g., preventing the pro-substrate from being utilized by the protein sensor) and functional utility (e.g., capable of being removed or altered by some intracellular agent, event, or response). The R group is removed or modified by an enzyme or molecule that may be attributed to an event or response (e.g., intracellularly, extracellularly, etc.) thereby creating a substrate for the firefly luciferase. Some suitable pro-substrates for a firefly luciferase enzyme (or modified version thereof) may comprise incomplete luciferin (e.g., missing a chemical group or moiety) which becomes the luciferin substrate upon addition of the missing element by a cellular event, agent, condition, etc. In certain embodiments, irrespective of the identity of the pro-substrate, once converted into the substrate (e.g., pro-luciferin or a pro-luciferin derivative), the substrate exits (e.g., diffuses from) the cell and is utilized by the protein sensor to generate a signal (e.g., bioluminescence). Using this method, cellular responses are measured in real time over an extended period of time.

In some embodiments, the method comprises contacting a living cell with a protein sensor comprising a coelenterazine-utilizing luciferase enzyme (e.g., *Renilla* luciferase or *Oplophorus* luciferase) and a pro-coelenterazine or pro-coelenterazine derivative substrate. In some embodiments, the pro-coelenterazine or pro-coelenterazine derivative substrate comprises a coelenterazine moiety (or coelenterazine derivative moiety) and a blocking moiety that prevents the protein sensor from utilizing coelenterazine as a substrate. In such embodiments, removal or alteration of the blocking group results in a substrate (e.g., coelenterazine or modified coelenterazine) that can be utilized by the protein sensor to produce a signal. In other embodiments, the pro-coelenterazine or pro-coelenterazine derivative substrate comprises a modified coelenterazine. In such embodiments, alteration of the modified coelenterazine results in a substrate (e.g., coelenterazine or an active modified coelenterazine) that can be utilized by the protein sensor to produce a signal. In some embodiments, a pro-substrate comprises an R group (e.g., organic moiety, peptide, nucleic acid, etc.) that prevents the pro-substrate from being utilized by the protein sensor to produce a signal. In some embodiments, the R group comprises both blocking functionality (e.g., preventing the pro-substrate from being utilized by the protein sensor) and functional utility (e.g., capable of being removed or altered by some intracellular agent, event, or response). The R group is removed or modified by an enzyme or molecule that may be attributed to a cellular event or response thereby creating a substrate for the coelenterazine-utilizing luciferase enzyme. Some suitable pro-substrates for a coelenterazine-utilizing luciferase enzyme (or modified version thereof) may comprise incomplete coelenterazine (e.g., missing a chemical group or moiety) which becomes the coelenterazine substrate upon addition of the missing element by a cellular event, agent, condition, etc. In certain embodiments, irrespective of the identity of the pro-substrate, once converted into the substrate (e.g., pro-coelenterazine or a pro-coelenterazine derivative), the substrate exits (e.g., diffuses from) the cell and is utilized by the protein sensor to generate a signal (e.g., bioluminescence). Using this method, cellular responses can be measured in real-time and/or continuously over an extended period of time.

In some embodiments, methods described herein provide real-time and/or continuous monitoring of cell viability. In some embodiments, real-time monitoring of cell viability comprises contacting a sample comprising a living cell with a protein sensor and a pro-substrate wherein the pro-substrate is converted inside a living cell to a substrate for the protein sensor. In some embodiments, the reducing intracellular environment of a living cell converts the pro-substrate into a substrate. The signal generated by the utilization of the substrate by the protein sensor is proportional to the number of living cells. In some embodiments, cell viability is measured for an extended period of time, e.g., 1, 2, 4, 24, 48, 72 hours, or more. When using assays described herein to measure cell viability, changes in the number of living cells are observable in real time (e.g., with a short (e.g., <10 minutes, <1 minute, <10 seconds) lag time).

In some embodiments, the non-accumulation of substrate in the assays described herein results in only presently-produced substrate being available for the protein sensor. When the number of living cells decrease, the amount of substrate also decreases, which is detectable as a decrease in the signal generated by the protein sensor. Due to predictable lag times between pro-substrate conversion and substrate utilization, changes in detectable signal can be readily correlated to the timing of changes in cell viability. Likewise, increases in detectable signal correlate, in real-time, to increases in cell number. Other assays utilizing stable substrates and/or allowing for substrate accumulation cannot provide the same real-time readout of increases and decreases in cell population.

In some embodiments, the method comprises real-time measurement of enzyme activity inside a cell, e.g., caspase, protease, reactive oxygen species, cytochrome P450 (CYP450) enzyme, monoamine oxidase (MAO), etc. activity. In some embodiments, the method comprises the real-time measurement of caspase activation within a cell, e.g., caspase-2, caspase-3/7, caspase-6, caspase-8, or caspase-9. In some embodiments, the method comprises real-time measurement of caspase activation comprising contacting a living cell with a protein sensor and a pro-substrate for the caspase enzyme. In some embodiments, the pro-substrate comprises a pro-furimazine, e.g., Formula I, wherein R is a peptide recognition sequence for the caspase, e.g., VDVAD (SEQ ID NO: 3), DEVD (SEQ ID NO: 4), VEID (SEQ ID NO: 5), LETD (SEQ ID NO: 6), or LEHD (SEQ ID NO: 7). In some embodiments, the pro-substrate comprises a pro-coelenterazine or pro-luciferin. In some embodiments, the method comprises real-time measurement of caspase activation comprising contacting a living cell with a protein sensor and a pro-substrate for the caspase enzyme.

In some embodiments, the method comprises real-time measurement of intracellular conditions (e.g., redox state, pH, etc.). In such embodiments, a pro-substrate is provided that is sensitive to particular conditions (e.g., oxidative stress) and is converted into a substrate in the presence of such conditions. Conditionally-sensitive pro-substrates are converted into unstable and/or non-accumulating substrates providing a real-time readout of intracellular conditions.

In some embodiments, the methods described herein can be combined with other assay methods, e.g., cell viability, cytotoxicity, reporter gene assay. In some embodiments, the method described herein identifies the most optimal time for performing such functional assays. In some embodiments, the method described herein is combined with a fluorescent assay. In other embodiments, the method described herein is combined with a luminescent assay. In some embodiments, the method described herein provides a self-contained and/or homogeneous assay.

In some embodiments, methods described herein can be multiplexed to detect two or more different events, conditions, responses, and/or agents in real-time (e.g., using two or more different signals or locations or via other mechanisms). Examples of such multiplexing are provided in Examples 14 and 15. The present invention is not limited by the combinations of signals and cellular events that may be utilized in multiplex assays.

In some embodiments, the method comprises contacting a tissue or tissue sample with a protein sensor and a pro-substrate. In some embodiments, the method comprises administering a protein sensor and a pro-substrate to an animal, e.g., mouse or rat. In some embodiments, the method comprises contacting a bacterial cell or bacterial cell culture with a protein sensor and pro-substrate.

In embodiments described herein, one or more of the pro-substrate and substrate are capable of entering and/or exiting cells. Such entry and exit may occur by any suitable mechanism including, but not limited to passive diffusion, osmosis, active transport, endocytosis, phagocytosis, exocytosis, etc. The methods described herein are not limited by the means of various materials passing into and out of cells, and an understanding of what mechanisms are used or how they function is not required to practice the invention.

Any of the compositions useful in carrying out embodiments of the present invention (e.g., protein sensor, pro-substrates, buffers, cells, controls, etc.), alone or in combination with other compositions, may be provided in the form of a kit. For example, protein sensor and pro-substrate may be provided in a kit for detection of a cellular condition (e.g., cell viability). Kits may further comprise appropriate controls (e.g., negative, positive), containers, and/or detection reagents.

In certain embodiments, the signal is detected by any suitable device, detector, apparatus, system, etc. Depending upon the detectable signal (e.g., luminescence, colorimetric, etc.), and, for example, the assay conditions (e.g., multiplex, diagnostic conditions, etc.), suitable detectors may include, but are not limited to: CCD cameras, video cameras, photographic film, laser scanning devices, fluorometers, photodiodes, quantum counters, epifluorescence microscopes, scanning microscopes, flow cytometers, fluorescence microplate readers, or a fluorescence microscope. In some embodiments, detection is by real-time monitoring, end-point reads, sequential reads (e.g., every: 1 second, 2 seconds, 5 seconds, 10 seconds, 30 seconds, 1 minute, 2 minutes, etc.), or any other suitable detection/monitoring scheme.

In particular embodiments, methods are provided for multiplexing detection of different cellular events, conditions, and/or responses. Multiplex experiments may utilize end-point detection, real-time detection, continuous monitoring etc. In some embodiments, different detection methods are utilized (e.g., fluorescence, luminescence). In some embodiments, multiplex assays measure diverse cellular responses (e.g., apoptosis, reporter gene expression, metabolite assays, etc.). Examples of such multiplexing are provided in Examples 14 and 15. The present invention is not limited by the combinations of signals and cellular events that may be utilized in multiplex assays.

In some embodiments, a computer-based analysis program is used to correlate the raw data generated by the detection assay (e.g., the presence, absence, or amount of signal) into the concentration of an agent of interest or the magnitude, frequency and/or concentration of an event, condition, and or response related to that agent. The data may be reported in any suitable format (e.g., raw signal data, converted signal, agent concentration, event frequency, cellular conditions, etc.). The data may be stored (e.g., in a computer-readable format), displayed (e.g., on a monitor), printed, reported, etc. In some embodiments, methods provide computer-assisted analysis of the data (e.g., raw or correlated).

Various modifications of the described features and embodiments will be apparent to those skilled in the art without departing from the scope and spirit of the invention. Although specific embodiments have been described, it should be understood that the invention as claimed should not be unduly limited to such specific embodiments. For example, the present invention finds use with protein sensors, substrates, pro-substrates, and biological systems that are not explicitly mentioned herein. Indeed, various modifications of the described modes and embodiments are intended to be within the scope of the following claims.

EXPERIMENTAL

Example 1: General Assay Set Up for Continuous, Real-Time Monitoring of an Intracellular Event A pro-substrate and protein sensor are supplied to live cells. The pro-substrate enters the cells and is converted to a substrate for the protein sensor by an intracellular event. The substrate does not produce any detectable signal until it exits the cell and is utilized by the protein sensor. The substrate is either rapidly used by the protein sensor to produce a "flash signal" or is degraded. The substrate does not accumulate outside of the cells. Therefore, the continuous production of signal depends on the continuous flow of the substrate from the live cells allowing the detection of intracellular events continuously in real-time as they occur in live cells (FIG. 1).

Example 2: Real-Time Monitoring of Signals Produced in Live Cells

A. A549 cells were plated into wells of a 384-well plate at 2,000 cells/well. 40 ng/ml NANOLUC luciferase protein sensor and 50 µM PBI-4600 pro-substrate were added to the cells either together or individually. In some cases, the protein sensor and pro-substrate were pre-mixed together and incubated in the presence or absence of cells. Luminescence was monitored at various time points on a Tecan Infinite 500 plate reader (FIG. 2A).

B. 40 uM PBI-4600 pro-substrate and 100 ng/ml NANOLUC luciferase protein sensor were added to cell culture media. Half of the mixture was added to wells in a 384-well assay plate that contained media only. The other half of the mixture was added to wells that contained 2,000 K562 cells/well. Luminescence was monitored at multiple time points on a Tecan M1000 plate reader (FIG. 2B).

Figure 2:
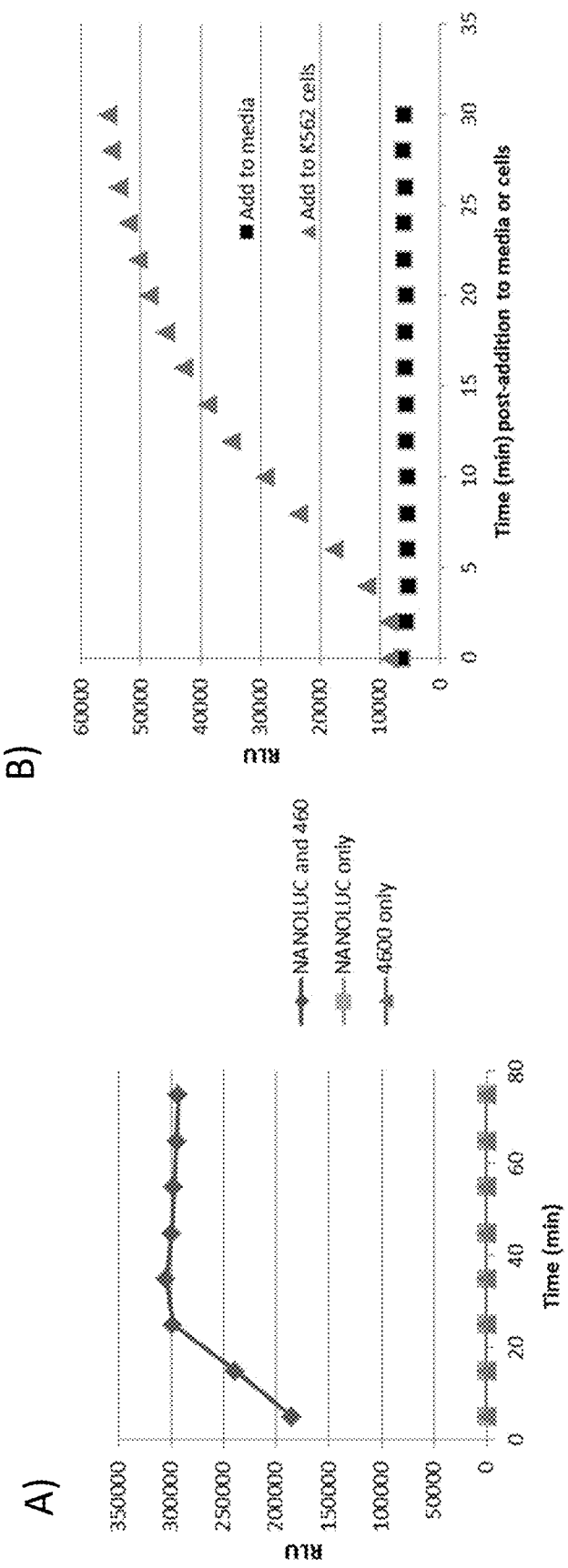
FIG. 2, panels A and B, illustrate that conversion of the pro-substrate to a substrate by live cells can be monitored outside the cells using the composition described herein.
Figure 3:
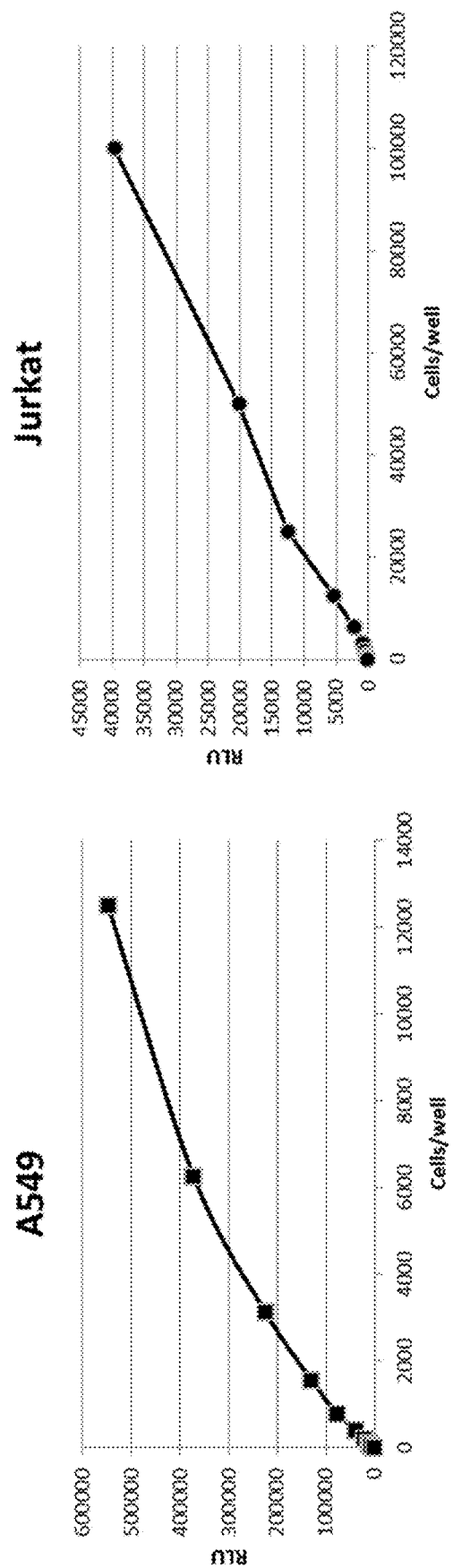
FIG. 3 illustrates that the signal generated using the method described herein is proportional to the number of live cells.

The results show that upon pro-substrate conversion to a substrate for the protein sensor by live cells, the protein sensor present outside the cells interacts with the substrate to produce a signal. The results also show that both components of the method described herein (the protein sensor and the pro-substrate), in the presence of live cells, are necessary to generate the signal (FIG. 2).

Example 3: Signal Generated by Live Cells is Proportional to the Number of Live Cells Jurkat or A549 cells were plated at different densities into wells of a 384-well assay plate. 50 µM PBI-4600 pro-substrate and 40 ng/ml NANOLUC luciferase protein sensor were added to the cells. After incubation at room temperature for 15 (A549) or 55 minutes (Jurkat), luminescence was measured on a Tecan Infinite 500 plate reader.

The results show that the signal generated using the method described herein increased proportionally with the increase in number of live cells present in the sample.

Example 4: Signal Instability

A549 cells were plated at 5,000 cells/well into wells of a 384-well assay plate. 50 µM PBI-4600 pro-substrate and 40 ng/ml NANOLUC luciferase protein sensor were incubated with the cells for 2 hours, and luminescence measured. 1% Triton X-100 was added to the cells, and luminescence measured 2 minutes post-addition.

Figure 4:
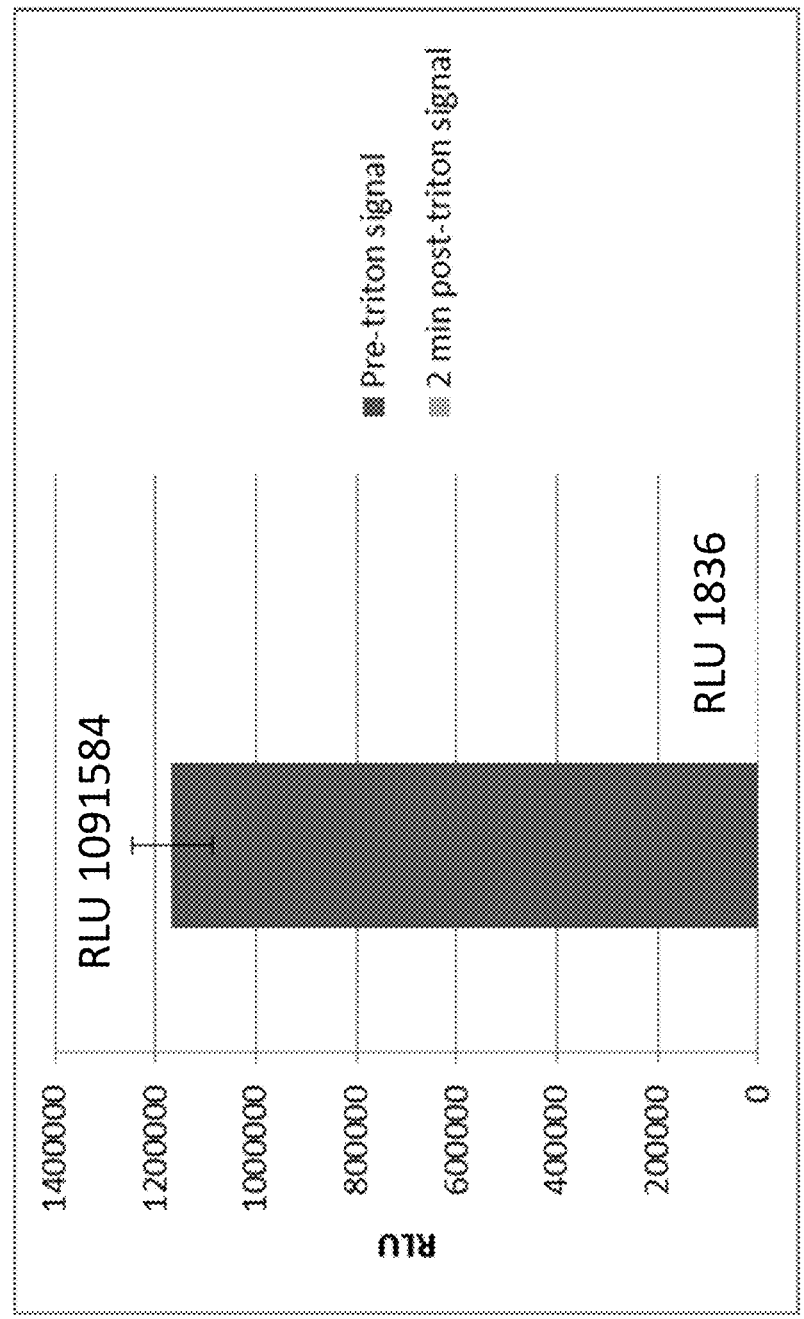
FIG. 4 illustrates that a rapid decrease in signal can be measured upon cell death using the method described herein.

The results demonstrate that the substrate/protein sensor-generated signal is not stable after cell death (FIG. 4).

Example 5: Measuring Cell Death in Real-Time

A549 cells were plated into wells of a 384-well plate at 1,000 cells/well in the presence of 40 µM PBI-4600 pro-substrate and 100 ng/ml NANOLUC luciferase protein sensor. The cells were incubated and the luminescence signal was monitored at various time points on a Tecan M1000 plate reader. Triton X-100 was then added to a final concentration of 1%, and compared to control cells that received media only. Luminescence was continually monitored.

Figure 5:
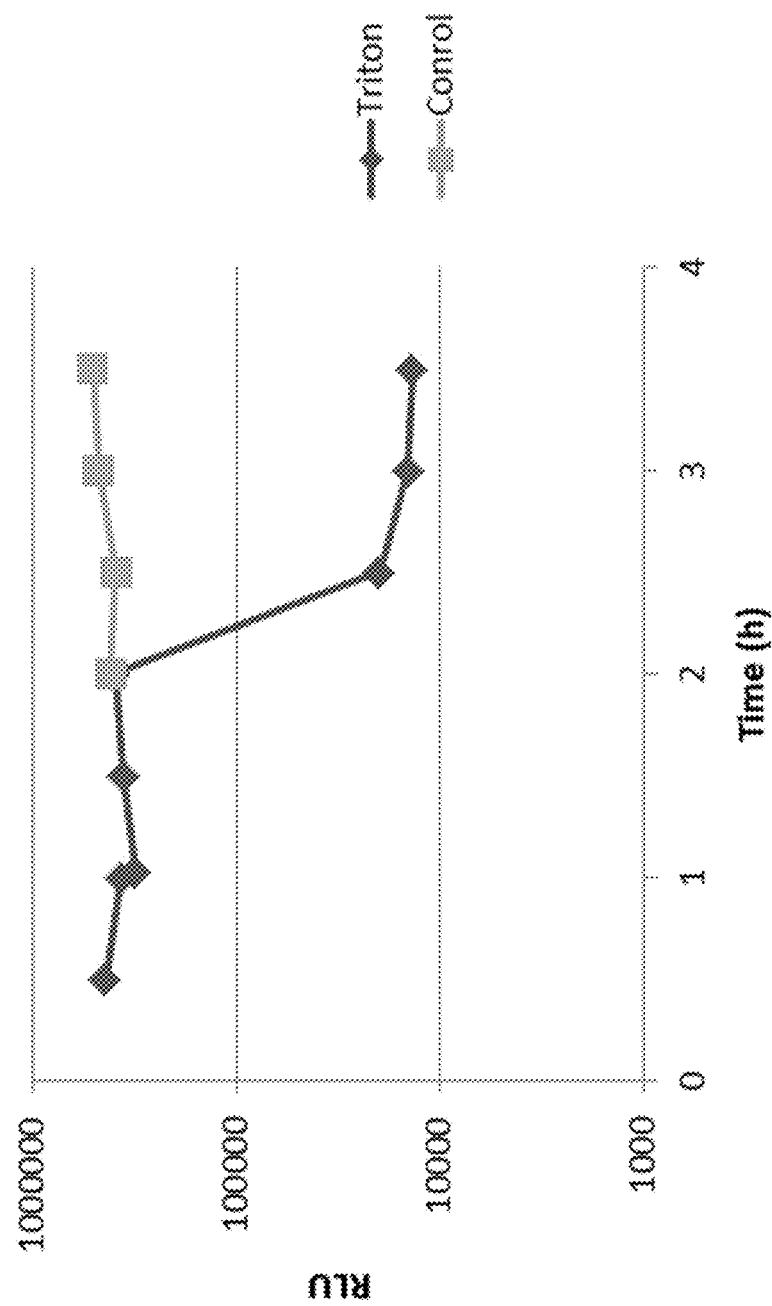
FIG. 5 illustrates that cell death can be monitored in real-time using the method described herein.

The results illustrate that while control cells continue to convert pro-substrate to substrate and generate light, Triton X-100 cells are no longer able to generate substrate due to cell death and a rapid decrease in signal is observed (FIG. 5).

Example 6: Comparison of Cell Viability Reagents

A549 cells were plated into wells of a 384-well plate at 1,000 cells/well. Cell viability reagents were added: 1x concentration of AlamarBlue or 40 µM PBI-4600 pro-substrate plus 100 ng/ml NANOLUC luciferase protein sensor, and the cells incubated for 120 minutes. Then, Triton X-100 was added to a final concentration of 1%. Luminescence and fluorescence (AlamarBlue: excitation 570 nm, emission 585 nm, bandwidths 5 nm) were measured on a Tecan M1000 plate reader at various time points (FIG. 6A).

A549 cells were plated into wells of a 384-well plate at 1,000 cells/well. Cell viability reagents were added: 1× concentration of AlamarBlue or 40 μM PBI-4600 pro-substrate and 100 ng/ml NANOLUC luciferase protein sensor. The cells were then incubated, and viability monitored at various time points as described above. Triton X-100 was then added to a final concentration of 1%, and cell viability was continually monitored (FIG. 6B).

Figure 6:
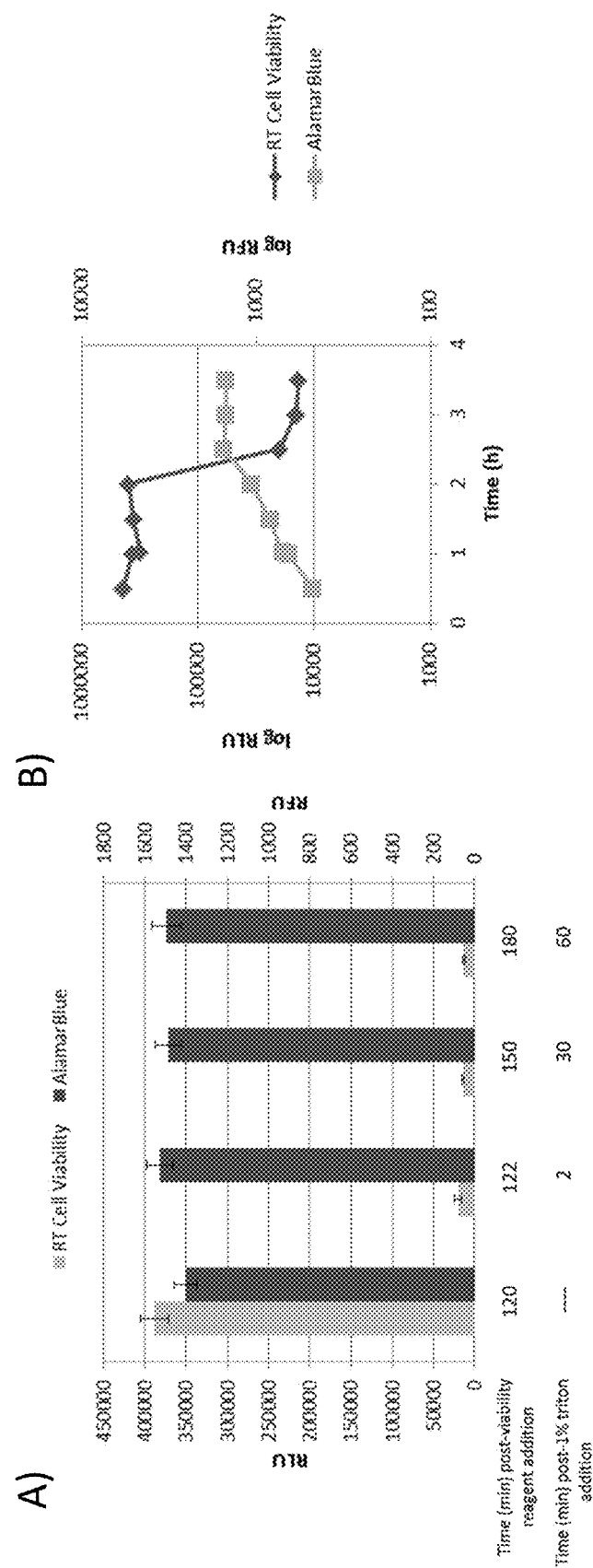
FIG. 6, panels A and B, illustrate that the ability of the method described herein to measure changes in real-time is a property not reported by other conventional assays.

The results demonstrate that the assay described herein is reactive in real-time to changes in live cells, a result that is not reported by conventional assays (FIG. 6).

Example 7: Reagent Effect on Cell Viability

A549 cells were plated into wells of a 384-well plate at 300 cells/well. A titration of PBI-4600 pro-substrate was added to the cells along with 40 ng/ml NANOLUC luciferase protein sensor. The interference of the assay components on cell viability was determined by monitoring the readout of a cytotoxicity assay (CellTox-Green, Promega Corporation) at various time points. At each time point, the fluorescence readout of cytotoxicity was measured on a Tecan M1000 plate reader (excitation 485 nm, emission 520 nm, bandwidths 5 nm).

Figure 7:
FIG. 7 illustrates that the pro-substrate and protein sensor do not interfere with cell viability.

The results illustrate that the presence of the reagents comprising the method described herein have no effect on cell viability (FIG. 7).

Example 8: Measuring Cell Proliferation

A549 cells were plated into wells of a 384-well plate at multiple densities (500, 250, 125, or 62.5 cells/well). 40 μM PBI-4600 pro-substrate and 100 ng/ml NANOLUC luciferase protein sensor were added to the cells. At various time points, luminescence was measured on a Tecan M200 plate reader with the gas control module (set at 37 C and 5% CO2). Readings were taken every 30 min for 72 hours.

Figure 8:
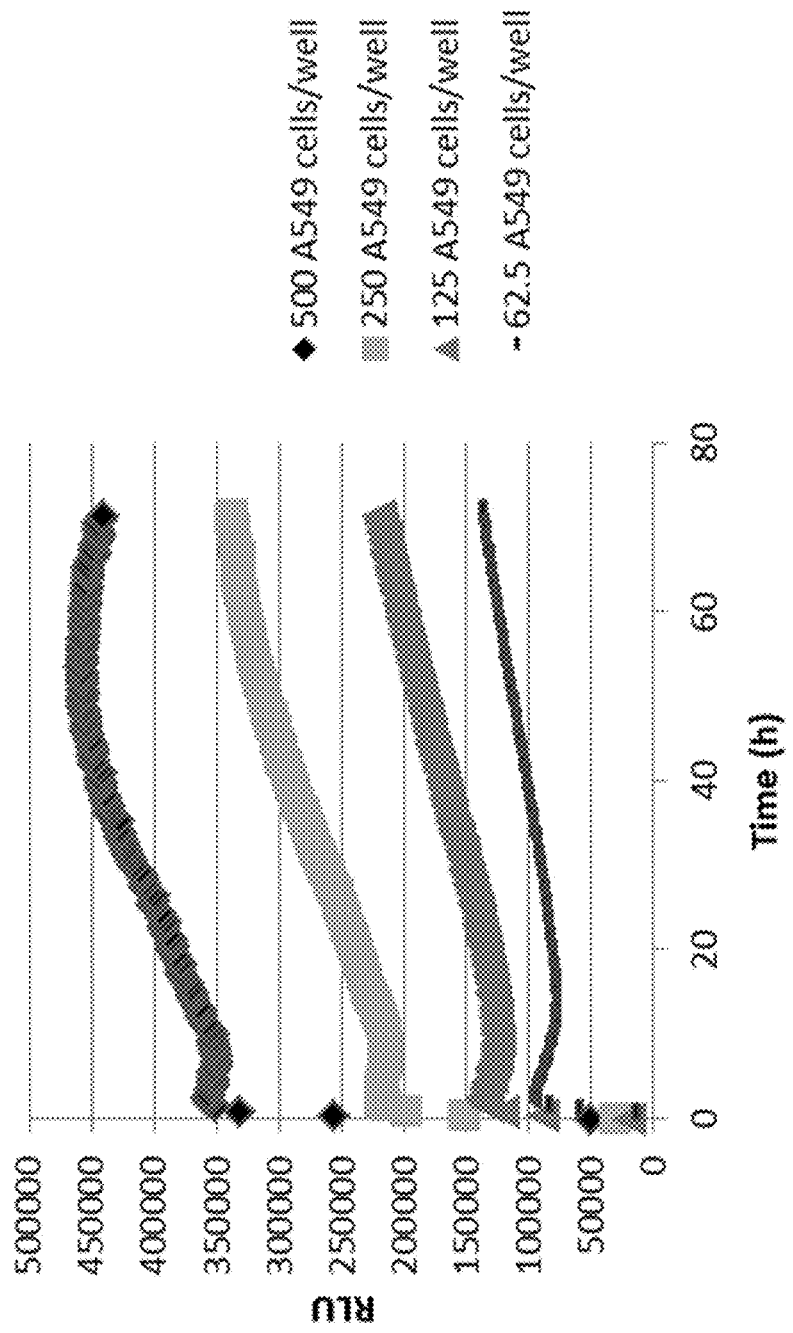
FIG. 8 illustrates the real-time dynamic monitoring of cell proliferation using the method described herein.

The results show the real-time increase in signal as cells continue to grow and proliferate (FIG. 8).

Example 9: Real-Time Measuring of Drug Induced Changes in Viability

Cardiomyocyte cells were plated and grown in media containing 40 uM PBI-4600 pro-substrate and 100 ng/ml NANOLUC luciferase protein sensor in a 37° C., 5% CO2 incubator. At various time points, luminescence was monitored on a Tecan M1000 plate reader. After multiple days of cell growth, digitonin was added to a final concentration of 200 μg/ml. Luminescence was read continually, starting immediately after digitonin addition.

Figure 9:
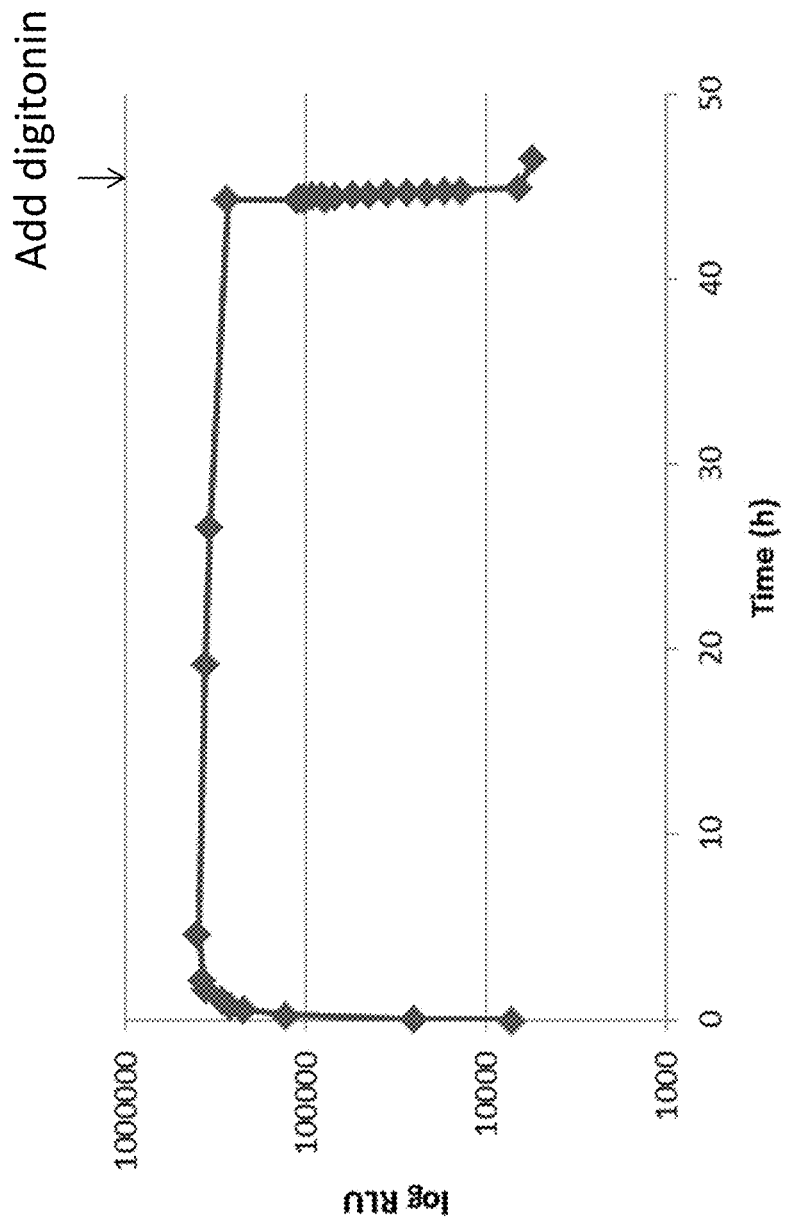
FIG. 9 illustrates the continuous real-time monitoring of induced changes in cell viability using the method described herein.

The results show that the cells are metabolically active and continue to produce a signal for multiple days. Addition of digitonin, a known agent to induce rapid cell death, results in rapid decrease in signal confirming the effect of the drug on live cells (FIG. 9).

Example 10: Determining the Optimal Timing of Pharmacological Responses

A) Response Depends on Drugs

Figure 10:
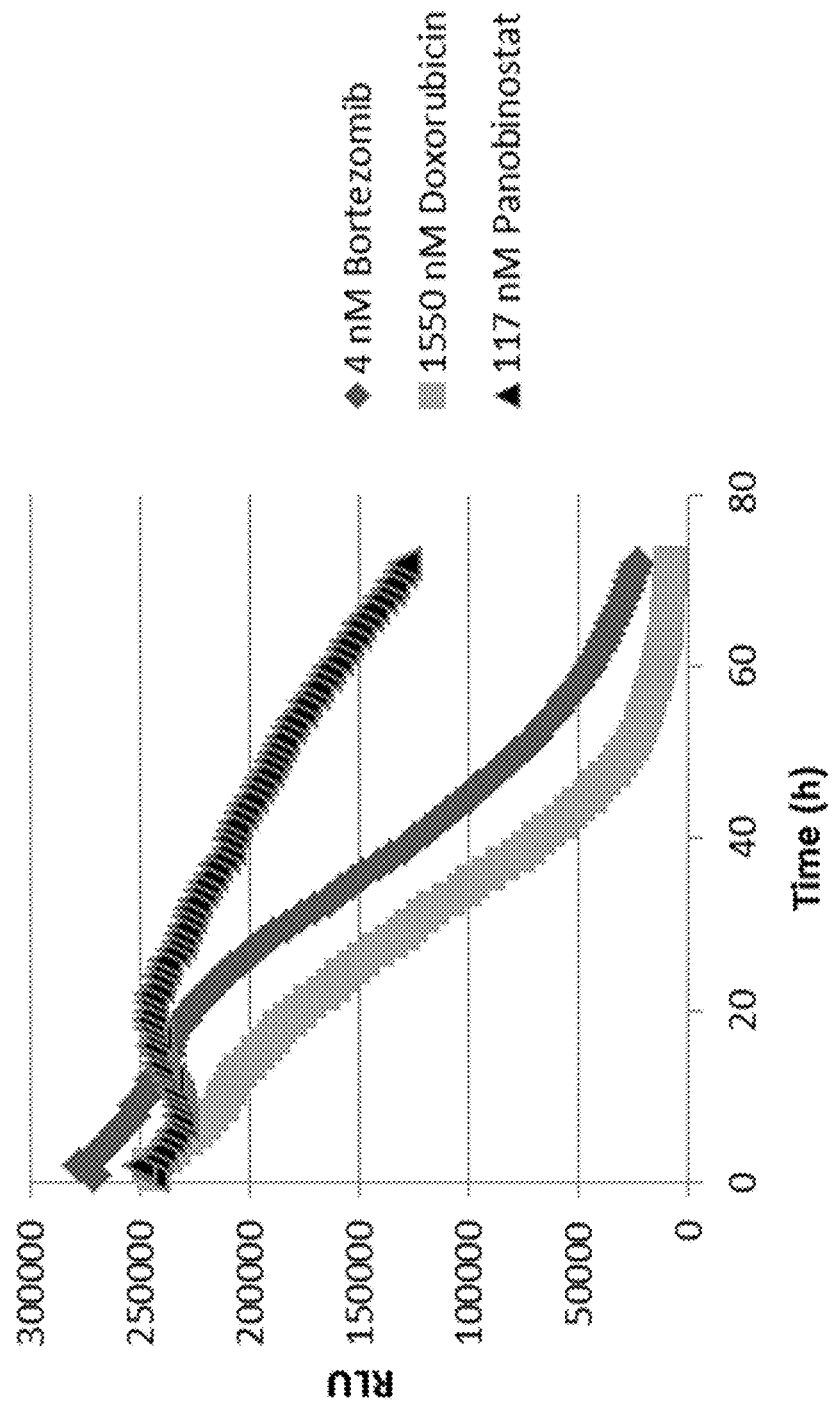
FIG. 10 illustrates the monitoring of the pharmacological response in real-time using the method described herein.

A549 cells were plated into wells of a 384-well plate at 250 cells/well in the presence of 40 μM PBI-4600 pro-substrate and 100 ng/ml NANOLUC luciferase protein sensor. Various drug compounds were added to the cells, and luminescence was monitored at various time points on a Tecan M200 plate reader with gas control module (settings: 37° C. and 5% CO2) using the same set of samples (FIG. 10).

B) Response Depends on Dose

Figure 11:
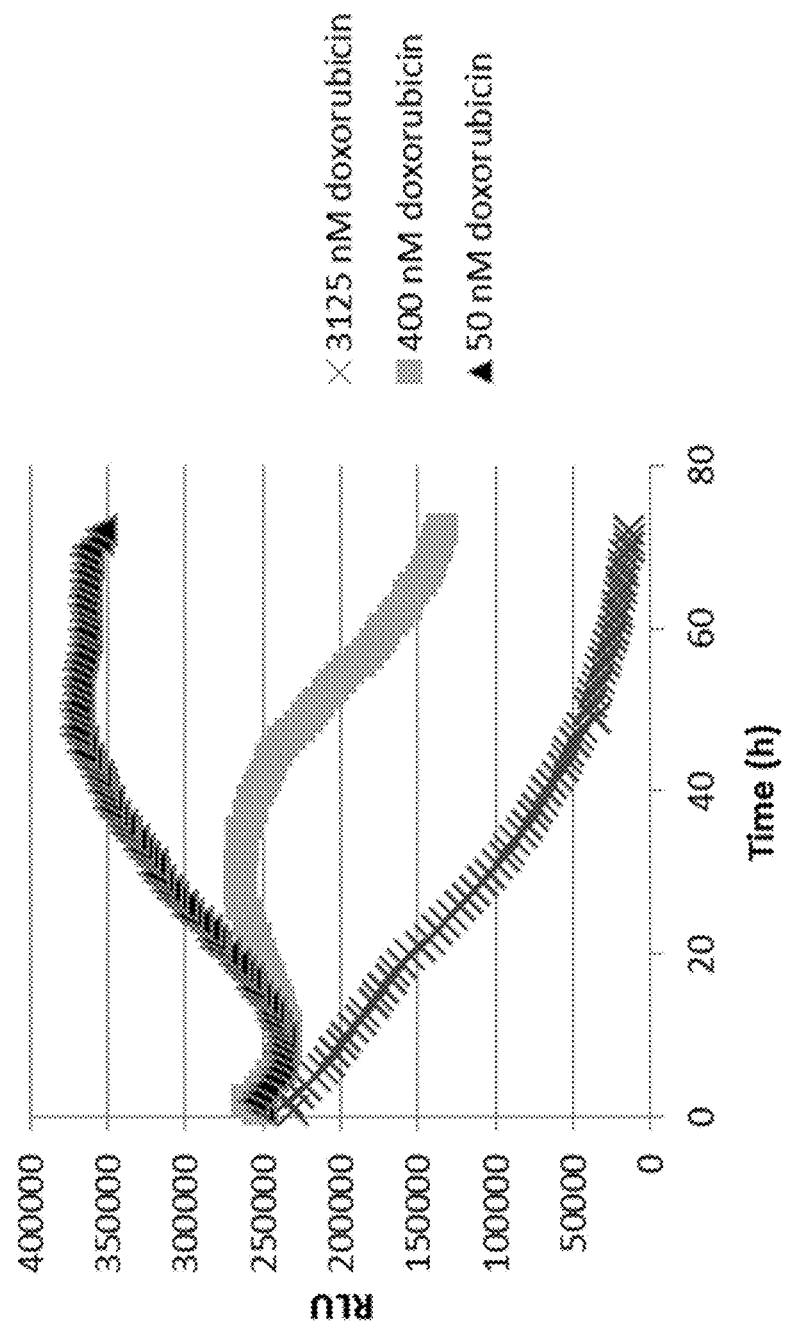
FIG. 11 illustrates determining the optimal timing of pharmacological responses using the method described herein.

A549 cells were plated into wells of a 384-well plate at 250 cells/well in the presence of 40 μM PBI-4600 pro-substrate and 100 ng/ml NANOLUC luciferase protein sensor. Doxorubicin was added to the cells at various concentrations, and luminescence monitored at multiple time points on a Tecan M200 plate reader with gas control module (settings: 37° C. and 5% CO2). (FIG. 11).

C) Response Depends on Cell Type

Figure 12:
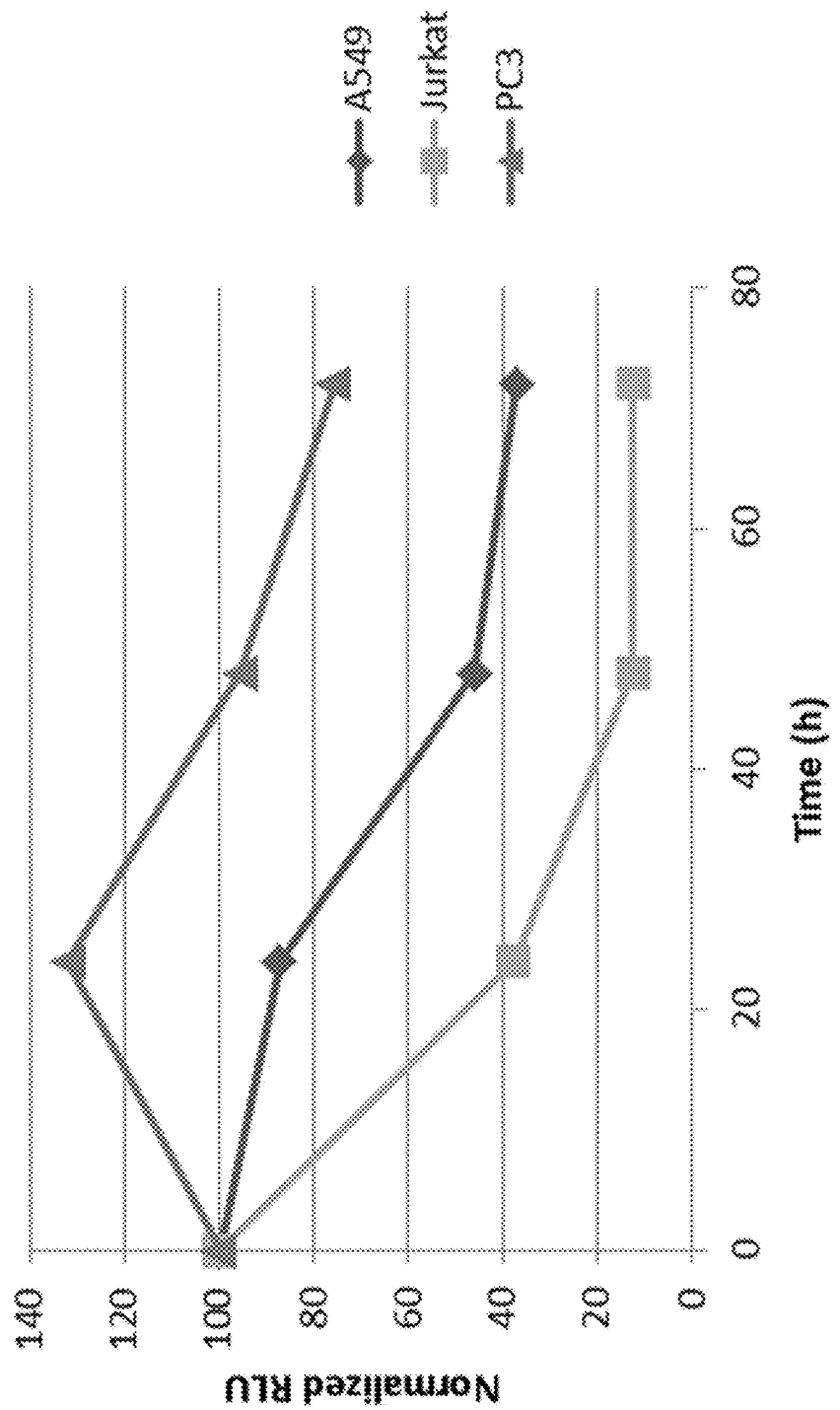
FIG. 12 illustrates that optimal time of responses depends on cell type using the method described herein.

A549, Jurkat and PC3 cells were plated into wells of a 384-well assay plate in the presence of 40 μM PBI-4600 pro-substrate and 40 ng/ml NANOLUC luciferase protein sensor. Doxorubicin (200 nM) was added to the cells, and luminescence measured at multiple time points on a Tecan M1000 plate reader. (FIG. 12)

The results in A-C show that continuous, real-time monitoring of cell viability allows examination of drug compound effect at different time points during treatment. The time of the response will differ depending on the drug compounds used (FIG. 10), the drug concentration (FIG. 11) and the cell type (FIG. 12). The method described herein allows detection of the time of the response by monitoring repeated reads using the same set of samples.

Example 11: Collecting Data at Different Time Points

Jurkat cells were plated at 6,000 cells/well into wells of a 384-well assay plate in the presence of 40 μM PBI-4600 pro-substrate and 40 ng/ml NANOLUC luciferase protein sensor. Doxorubicin was added to the cells at various concentrations, and luminescence measured at 24, 48, and 72 hours on a Tecan M1000 plate reader. IC50 values were determined by fitting the data to a nonlinear regression, sigmoidal dose-response (variable slope) curve using GraphPad Prism version 5.03.

Figure 13:
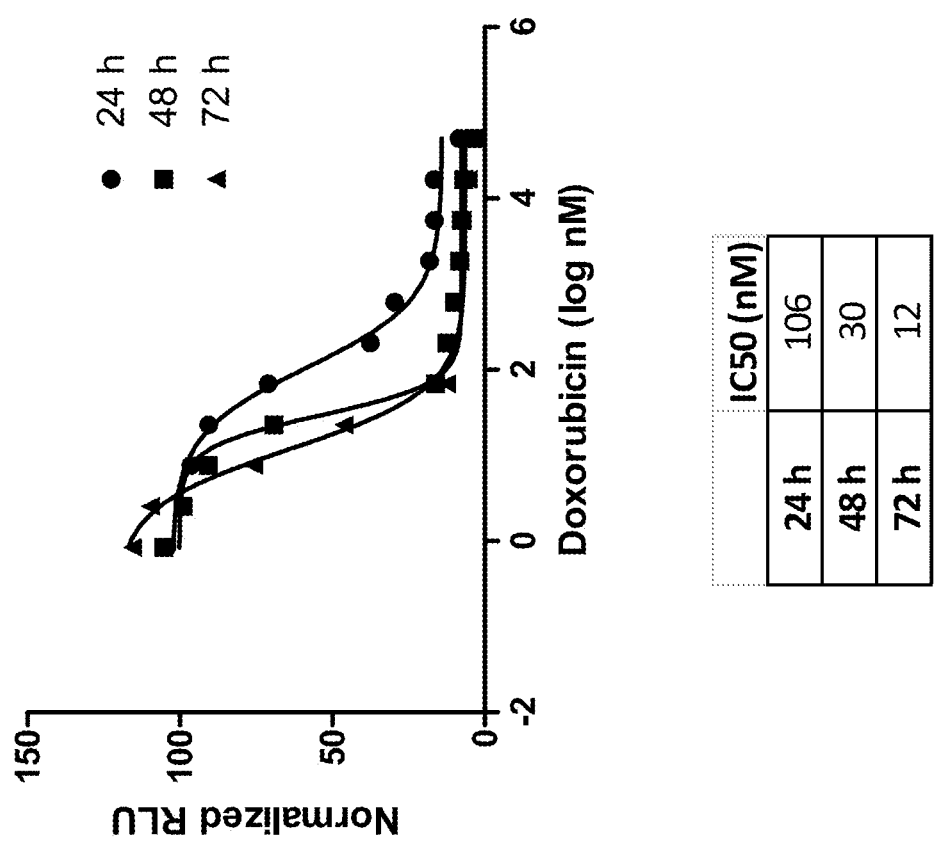
FIG. 13 illustrates the measurement of time-dependent changes in drug IC50 values using the same set of samples in the method described herein.

The results illustrate the ability of method described herein to measure changes in drug IC50 values during treatment using the same set of samples. In comparison, conventional endpoint assays require a separate set of samples must be generated for each individual time point (FIG. 13).

Example 12: Comparison of Pharmacological Responses

A549 cells were plated at 3,000 cells/well into wells of a 384-well assay plate. The cells were treated with a digitonin dose curve for 24 hours. MTS and CELLTITER-GLO reagents (Promega Corporation) were added to the cells after the 24 hour treatment according to manufacturer instructions. For the NANOLUC luciferase/4600 test wells, 50 μM PBI-4600 pro-substrate and 40 ng/ml NANOLUC luciferase protein sensor were co-incubated with digitonin for the full 24 hour time course. Luminescence was measured on a Tecan M1000 plate reader. MTS signals were measured by analyzing absorbance at 490 nm on the Tecan M1000 plate reader.

Figure 14:
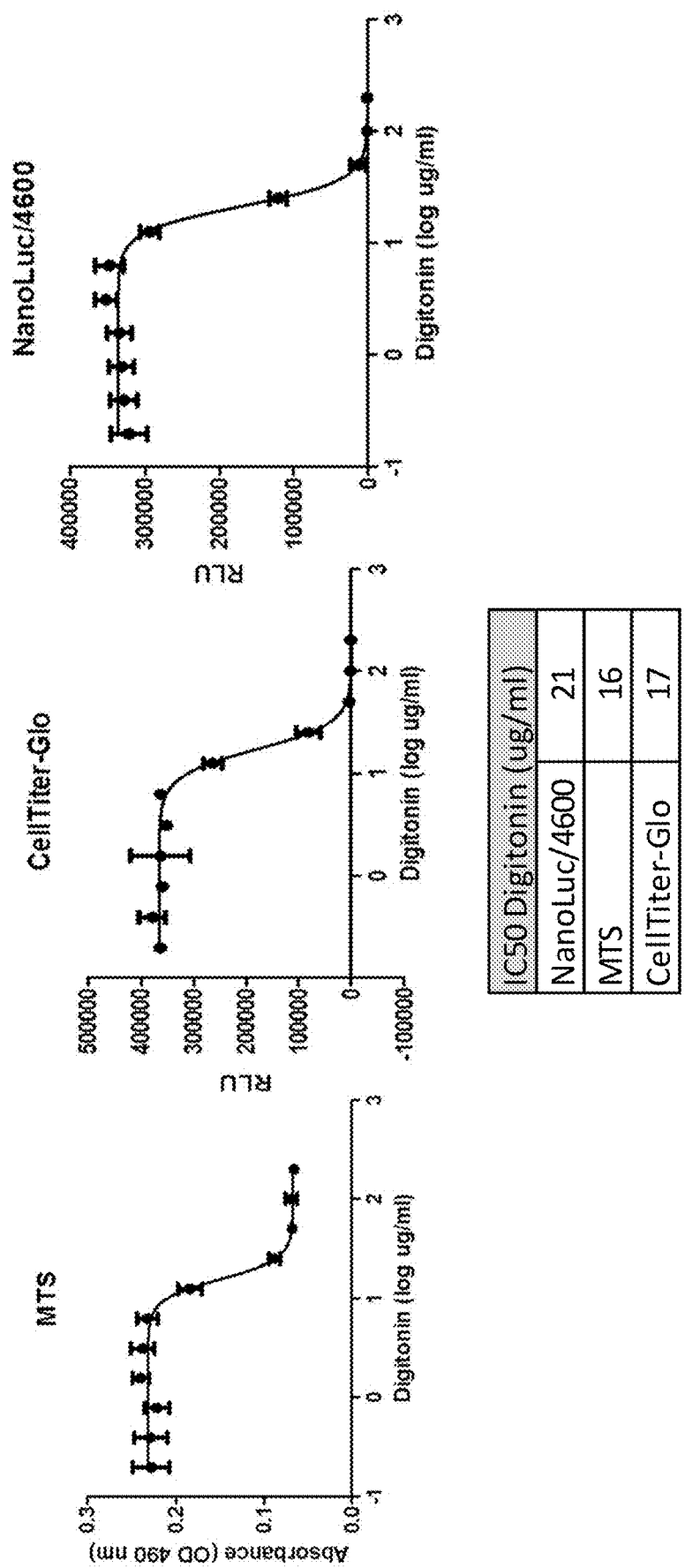
FIG. 14 illustrates responses determined using the method described herein are in agreement with other conventional methods.

The results demonstrate that IC50 values determined using the method described herein are in close agreement with the values obtained by well accepted endpoint assays (FIG. 14).

Example 13: Using the Real-Time Cell Viability Assay to Determine Optimal Time Points for Downstream Applications In this example, the real-time cell viability assay described herein was used to determine the optimal time point for measuring changes in NAD/NADH levels upon treatment with the NAD biosynthesis pathway inhibitor FK866. NAD/NADH are important cofactors that regulate cell metabolism and effect cell growth. To better understand the role of those nucleotides in cell function, it is important to establish the relationship between changes in NAD/NADH levels and cell survival.

K562 cells were plated into wells of a 384-well plate at 6000 cells per well in 25 ul media containing 40 ng/ml of protein sensor NANOLUC luciferase and 40 µM of pro-substrate PBI-4600 in the presence or absence of 0.5 µM FK866 compound. Luminescence was measured repeatedly using the same set of samples. The information was used to set up endpoint NAD/NADH detection assays (Promega Corporation) at the time point (21 hour) before cell viability was considerably compromised and the end of drug treatment.

Figure 15:
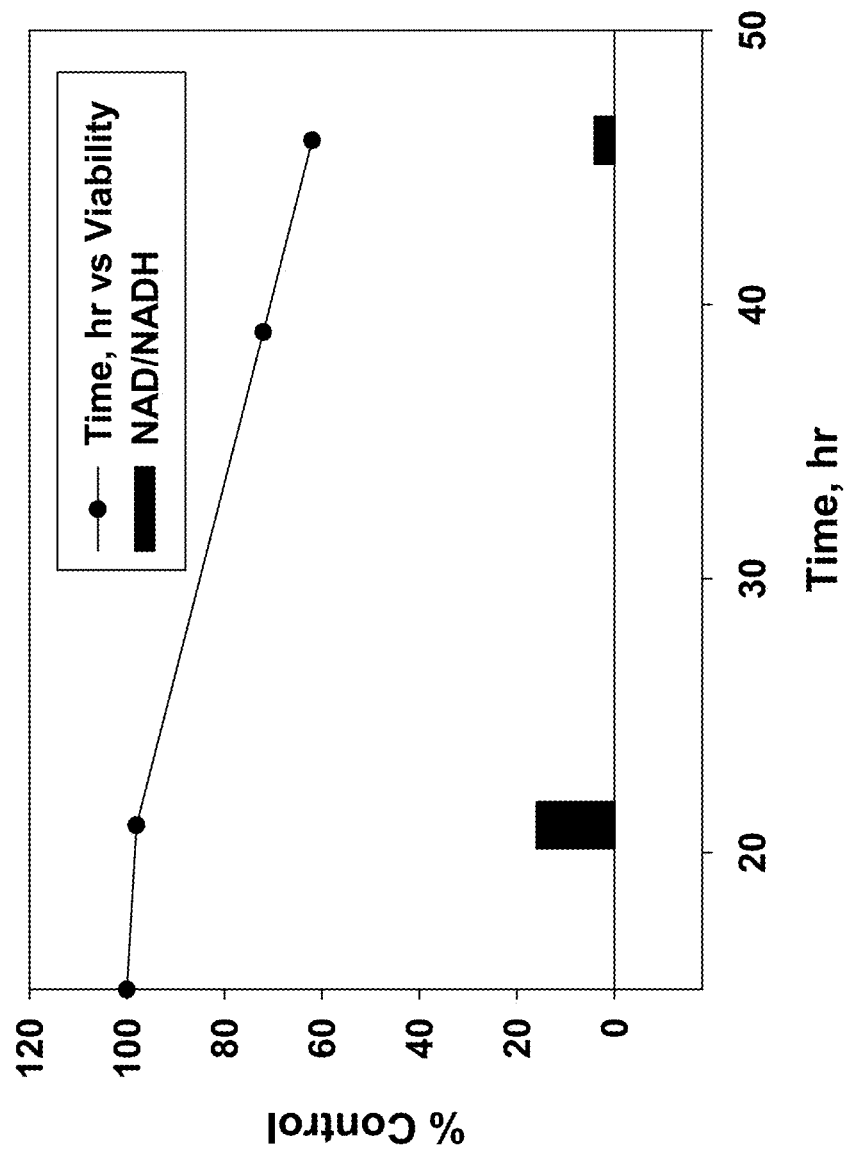
FIG. 15 illustrates the use of real time cell viability measurements for determining the optimal time points to perform end point downstream analysis.

The results show that by using the real-time cell viability assay, optimal time points for end point assays can be conveniently determined using one set of samples eliminating the need for setting up multiple samples at each time point (FIG. 15).

Example 14: Multiplexing with Luminescence Assay Methods

Current approaches for multiplexing bioluminescence assays require either the use of special filters or the inhibition of activity of the first reaction before the light generated by the second assay can be measured. In the method described herein, the signal depends on continuous substrate production by live cells and is rapidly decreased upon cell lysis which creates conditions where the luminescence signal from the second reaction can be measured directly without any additional requirements (e.g. the use of inhibitors or special filters).

A) Multiplexing Real-Time Cell Viability Monitoring with Caspase Activation Detection Jurkat cells were plated at 5,000 cells/well into wells of a 384-well assay plate. Either media (caspase activation) or 40 ng/ml NANOLUC luciferase and 50 µM PBI-4600 were then added to the cells. The samples were then treated with a TRAIL titration. Cell viability and caspase activation were monitored at multiple time points on a Tecan M1000 plate reader by first measuring luminescence from the cell viability assay, adding CASPASE-GLO 3/7 Assay reagents according to the manufacturer's instructions (Promega Corporation; quenches the signal from the viability assay), and measuring luminescence from the CASPASE-GLO 3/7 Assay.

Figure 16:
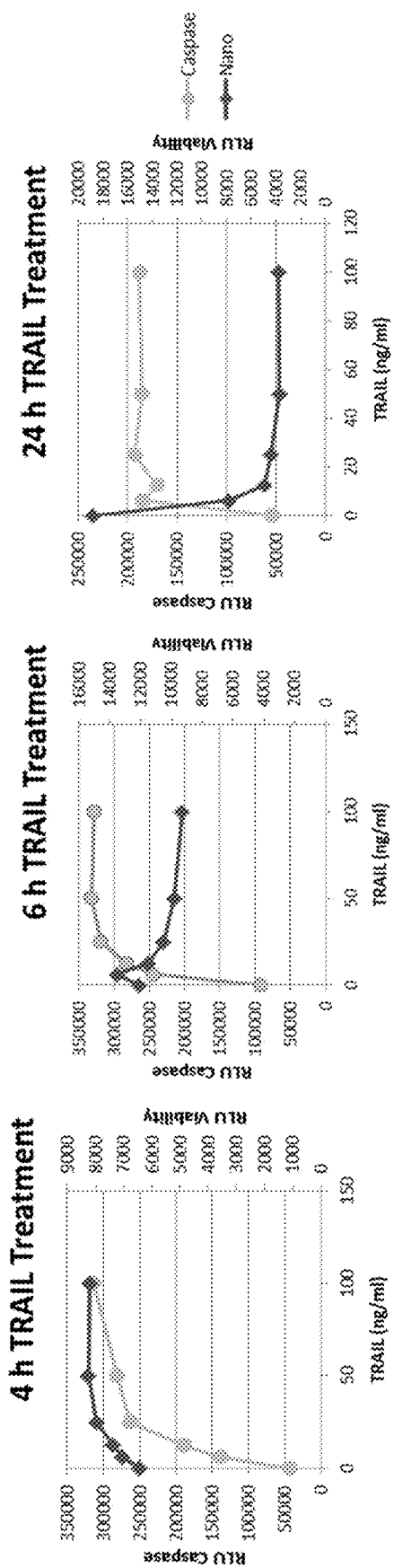
FIG. 16 illustrates the ability of the method described herein comprising a NANOLUC luciferase protein sensor and pro-furimazine substrate (PBI-4600) to be multiplexed with another luminescent assay, CASPASE-GLO 3/7 assay ("Caspase").

The results illustrate that induction of apoptosis by caspase activation leads to cell death. Cell death can be monitored in real-time by the method described herein, and the induction of apoptosis can be confirmed by multiplexing with other luminescent assays such as CASPASE-GLO 3/7 (FIG. 16).

B) Multiplexing Real-Time Cell Viability Monitoring with a Reporter Gene Assay

A cell titration of HEK cells stably expressing firefly luciferase was plated into wells of a 384-well assay plate. Media (reporter gene assay) or 40 ng/ml NANOLUC luciferase and 50 µM 4600 were then added to the cells. Cell viability was first measured as previously described, and then the ONE-GLO Luciferase Assay Reagent (Promega Corporation) was added according to the manufacturer's instruction. Luminescence from the firefly luciferase reporter was then measured on a Tecan M1000 plate reader.

Figure 17:
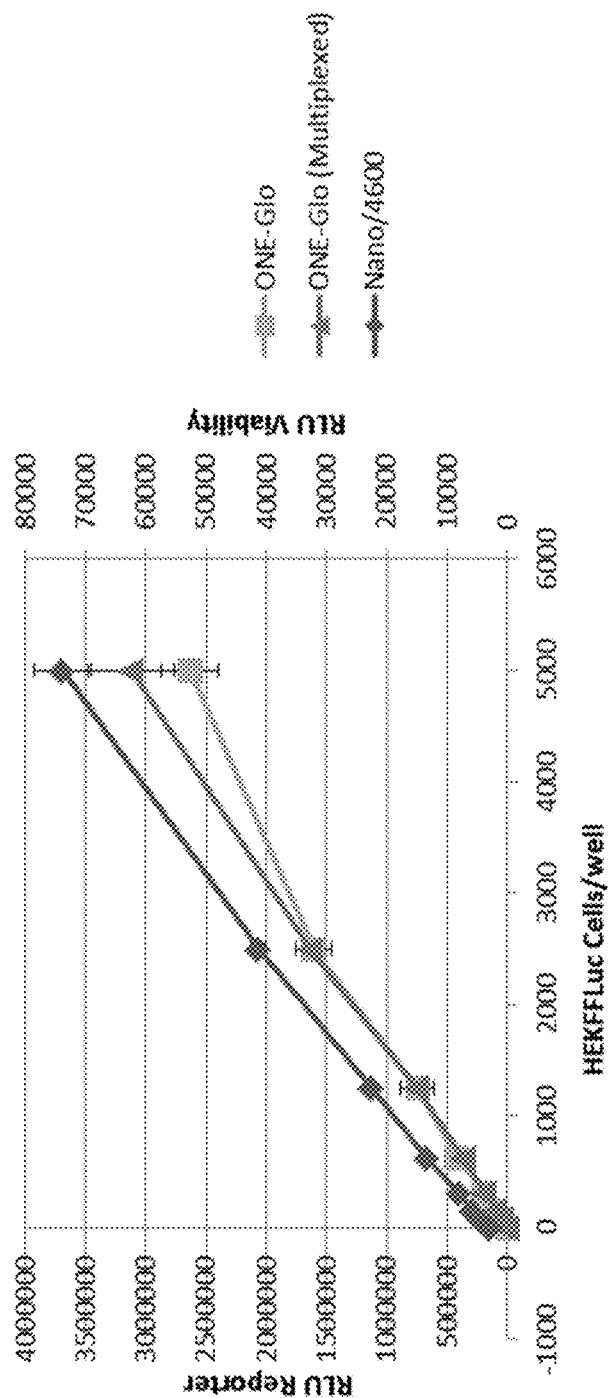
FIG. 17 illustrates the method described herein can be multiplexed with a reporter gene assay allowing normalization of the expression levels of the reporter to the number of live cells present in the sample.

The results demonstrate that the method described herein can be multiplexed with a reporter gene assay (FIG. 17), and the expression levels of the reporter can be normalized to the number of live cells present in the sample.

Example 15: Multiplexing with Fluorescence Assay Methods

A549 cells were plated at 300 cells/well into wells of a 384-well assay plate. 40 ng/ml NANOLUC luciferase and 50 µM PBI-4600 plus CELLTOX Green Cytotoxicity dye (Promega Corporation) were added to the cells. The cells were then treated with a digitonin dose curve and viability (luminescence) and cytotoxicity (fluorescence; excitation 485 nm, emission 520 nm, bandwidths 5 nm) were monitored over time on a Tecan M1000 plate reader.

Figure 18:
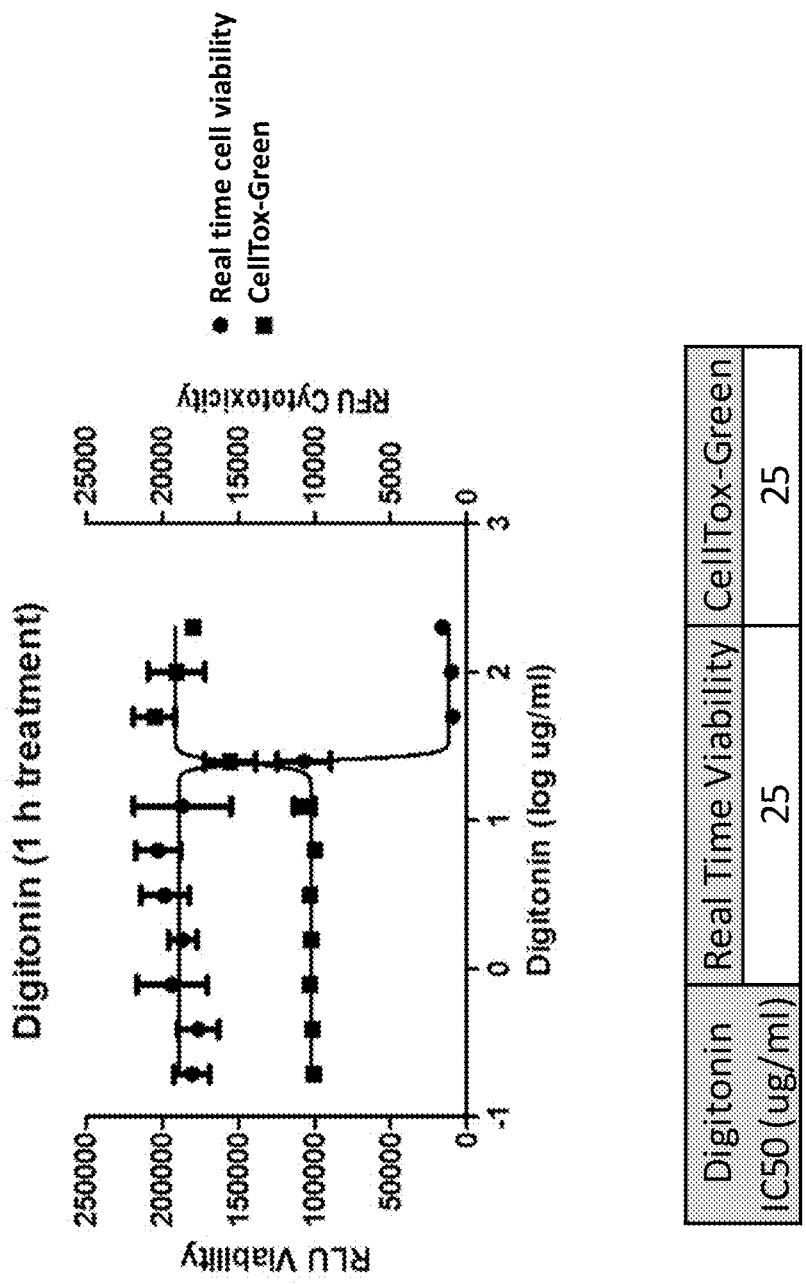
FIG. 18 illustrates that using the method described herein allows luminescence assays to be multiplexed with fluorescent assays in live cells.

Multiplexing fluorescence assays with end point (lytic) luminescence assays is a commonly used approach. These results demonstrate that by using the method described herein luminescence assays can be multiplexed with fluorescent assays in live cells (FIG. 18).

Example 16: Monitoring Drug Effect Over Extended Period of Time

A549 cells were plated at 500 cells/well into wells of a 384-well assay plate. 50 µM PBI-4600 pro-substrate, 40 ng/ml NANOLUC luciferase protein sensor and various concentrations of either doxorubicin or panobinostat (for generating dose curves) were added to the cells. Cell viability was determined at various time points by measuring the luminescent signal as previously described.

Figure 19:
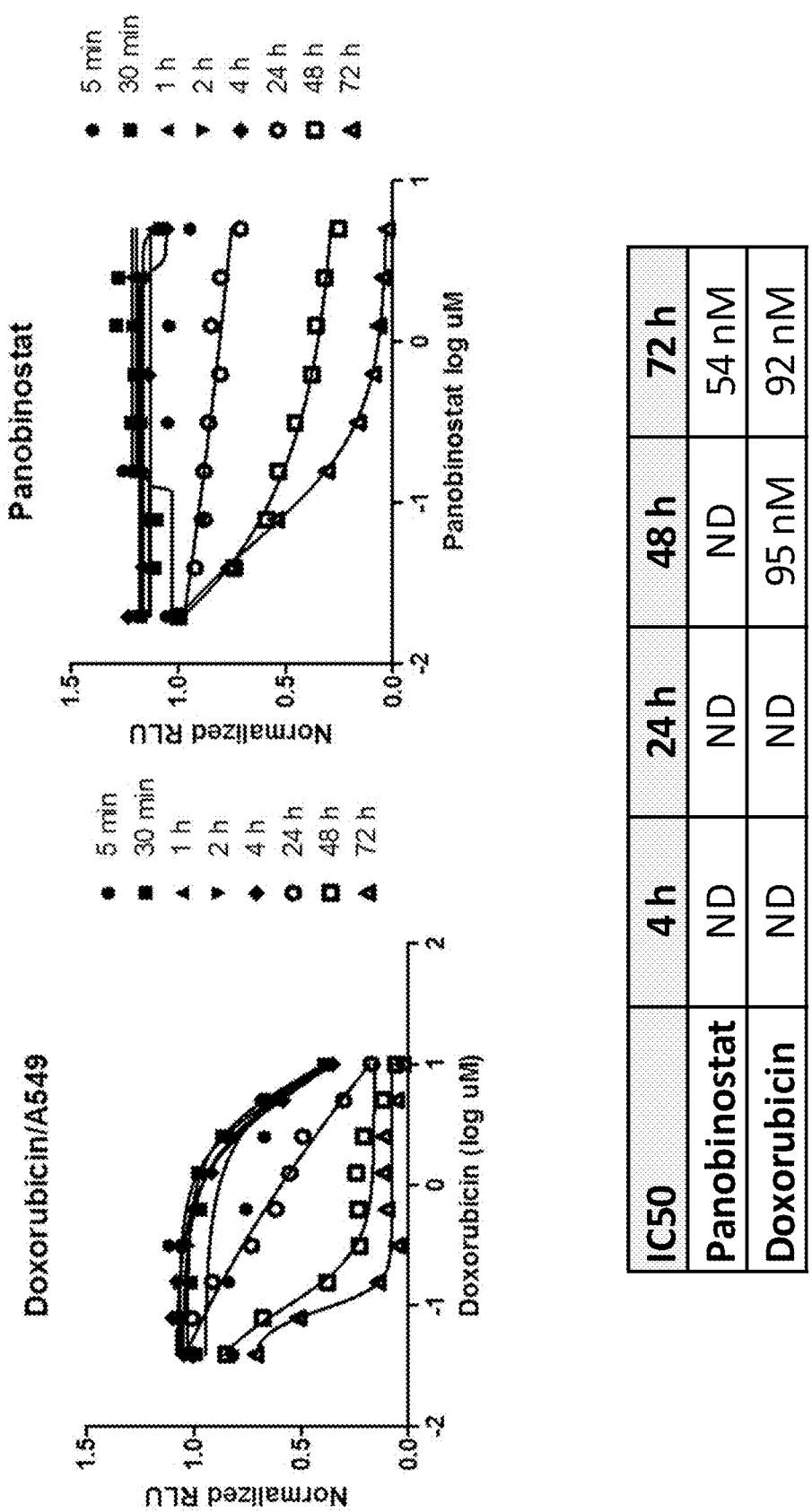
FIG. 19 illustrates the real-time monitoring of drug effect on cell viability over an extended period of time.

The results demonstrate that the method described herein can be used to monitor changes in cell viability in real-time for an extended period of time (FIG. 19).

Example 17: Using the Method as an Endpoint Assay

A549 cells were plated at 300 cells/well in a 384-well assay plate. The cells were treated with a panobinostat dose curve for 72 hours. Then, 50 µM PBI-4600 and 40 ng/ml NANOLUC luciferase protein sensor were added to the cells and incubated for 1 hour. Luminescence was measured on a Tecan M1000 plate reader.

Figure 20:
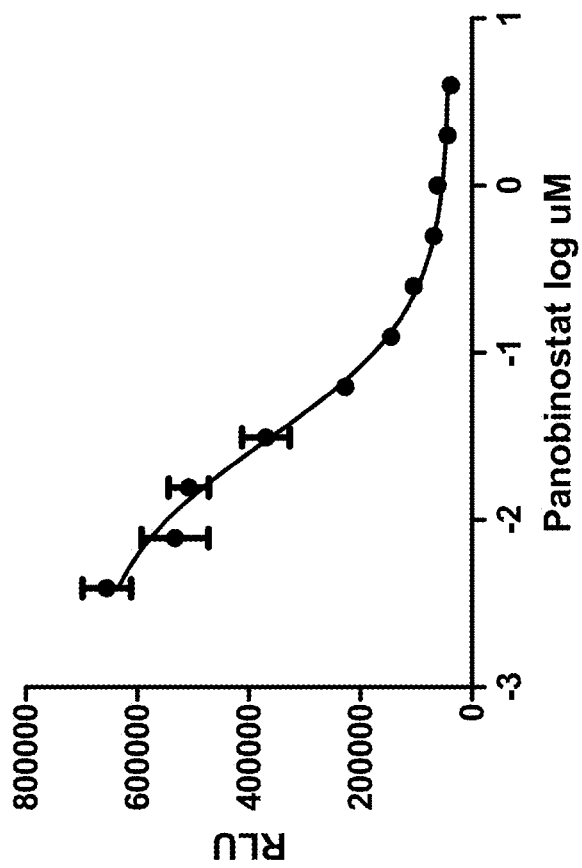
FIG. 20 illustrates that the method described herein can be used in an endpoint format.
Figure 21:
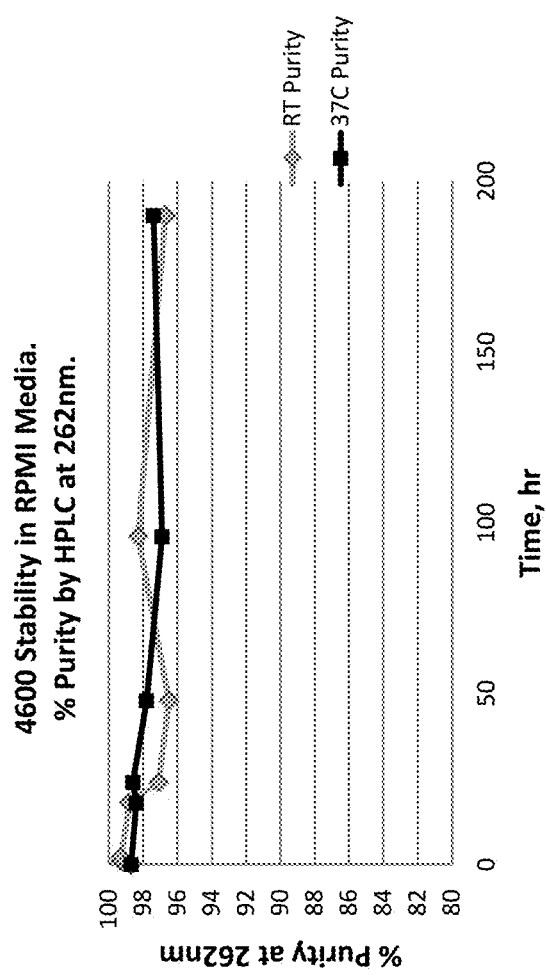
FIG. 21 illustrates the stability of the pro-furimazine substrate, PBI-4600.

The results illustrate that the method described can be used in an endpoint format (FIG. 20).

Example 18: Stability of the Pro-Furimazine Substrate, PBI-4600

PBI-4600 (50 µM) was incubated in RPMI cell culture media at room temperature (RT) or 37° C. for increasing time points, up to 190 hours. HPLC analysis was performed to determine the purity of PBI-4600 at various time points.

Figure 22:
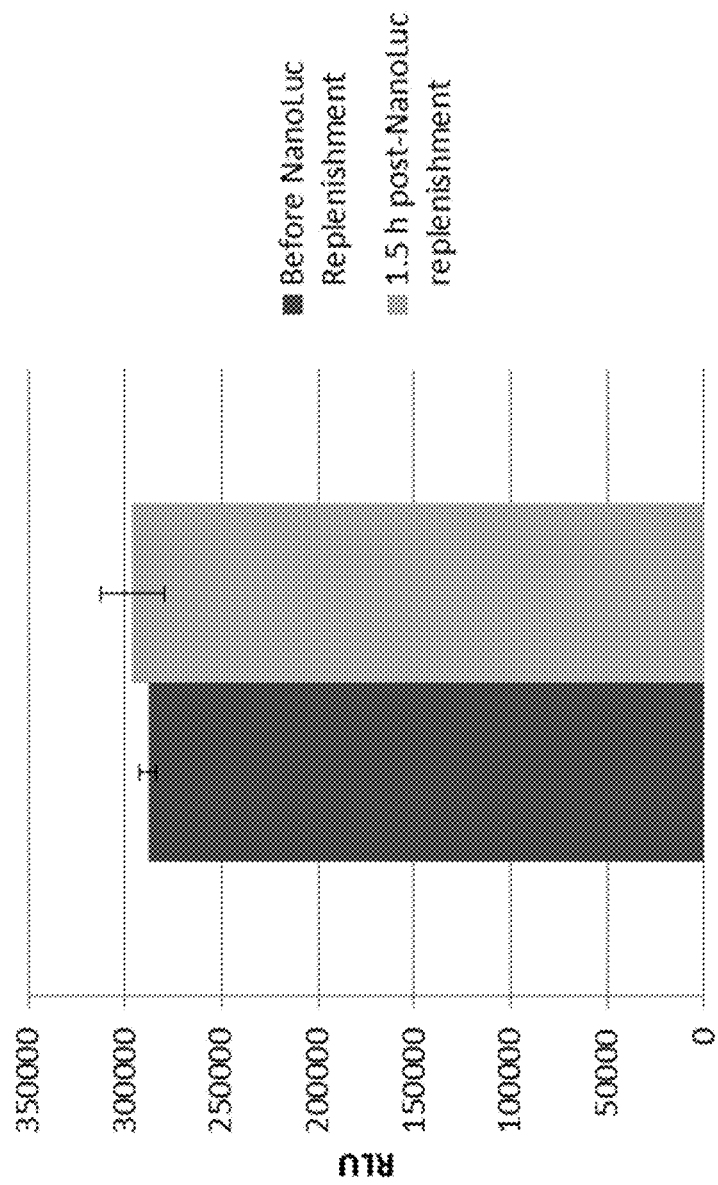
FIG. 22 illustrates the stability of the NANOLUC luciferase protein sensor in cell culture conditions for at least 72 hours.

The results demonstrate that PBI-4600 maintained greater than 90% purity for up to 190 hours (FIG. 22). The pro-substrate was not broken down or otherwise found to be unstable under these conditions.

Example 19: Protein Sensor Stability

A549 cells were plated at 250 cells/well into wells of a 384-well assay plate. 50 µM PBI-4600 pro-substrate and 40 ng/ml NANOLUC luciferase protein sensor were added to the cell culture and incubated for 72 hours. After incubation, 40 ng/ml NANOLUC luciferase protein sensor was added to the cell culture, and the signal was monitored 1.5 hours later.

Figure 23:
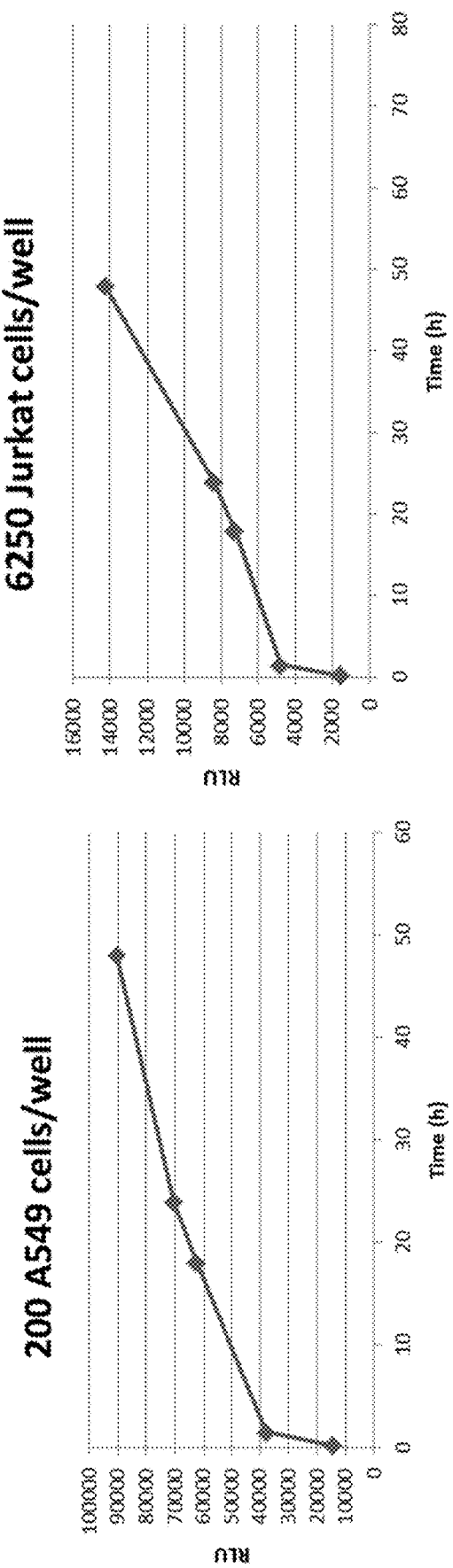
FIG. 23 illustrates real-time monitoring of cell proliferation using PBI-4601, a pro-coelenterazine substrate

The results demonstrate that the NANOLUC luciferase protein sensor added at time zero was still sufficient to generate a strong signal 72 hours later (FIG. 23). The addition of new NANOLUC luciferase protein sensor did not further increase this signal. Therefore, NANOLUC luciferase was stable in cell culture conditions for at least 72 h.

Example 20: Pro-Substrate PBI-4601, Coelenterazine Derivative

A549 (200 cells/well) or Jurkat (6250 cells/well) cells were plated into wells of a 384-well assay plate. 50 µM PBI-4601 pro-coelenterazine substrate and 40 ng/ml NANOLUC luciferase protein sensor were added to the cells. Luminescence was measured on a Tecan M1000 plate reader at various time points.

Figure 24:
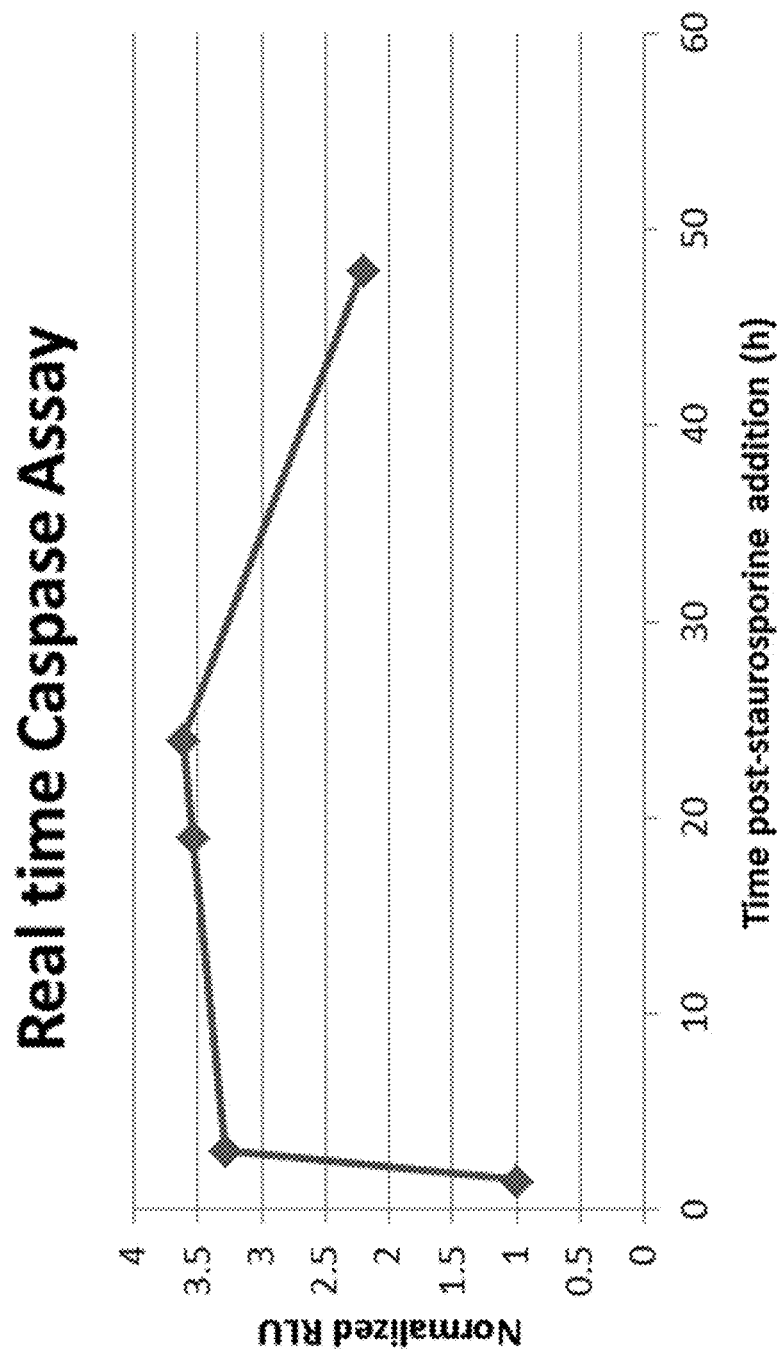
FIG. 24 illustrates real-time measurement of caspase activation using the method described herein comprising a NANOLUC luciferase protein and a pro-furimazine caspase probe (PBI-3741).

The results show real-time monitoring of cell proliferation using PBI-4601, a pro-coelenterazine substrate (FIG. 24).

Example 21: Real-Time Monitoring of Caspase Activation

A549 cells were plated at 1,000 cells/well into wells of a 384-well assay plate. 50 µM PBI-3741 (a pro-furimazine caspase substrate) and 40 ng/ml NANOLUC luciferase enzyme were added to the cells. To induce apoptosis, staurosporine was added to the cells at a 4 µM final concentration. The induction of apoptosis and activation of caspase were measured in real-time. The increase in pro-substrate to substrate conversion upon caspase activation was detected by the increase in luminescence during the time of staurosporine treatment using the method described herein.

Figure 25:
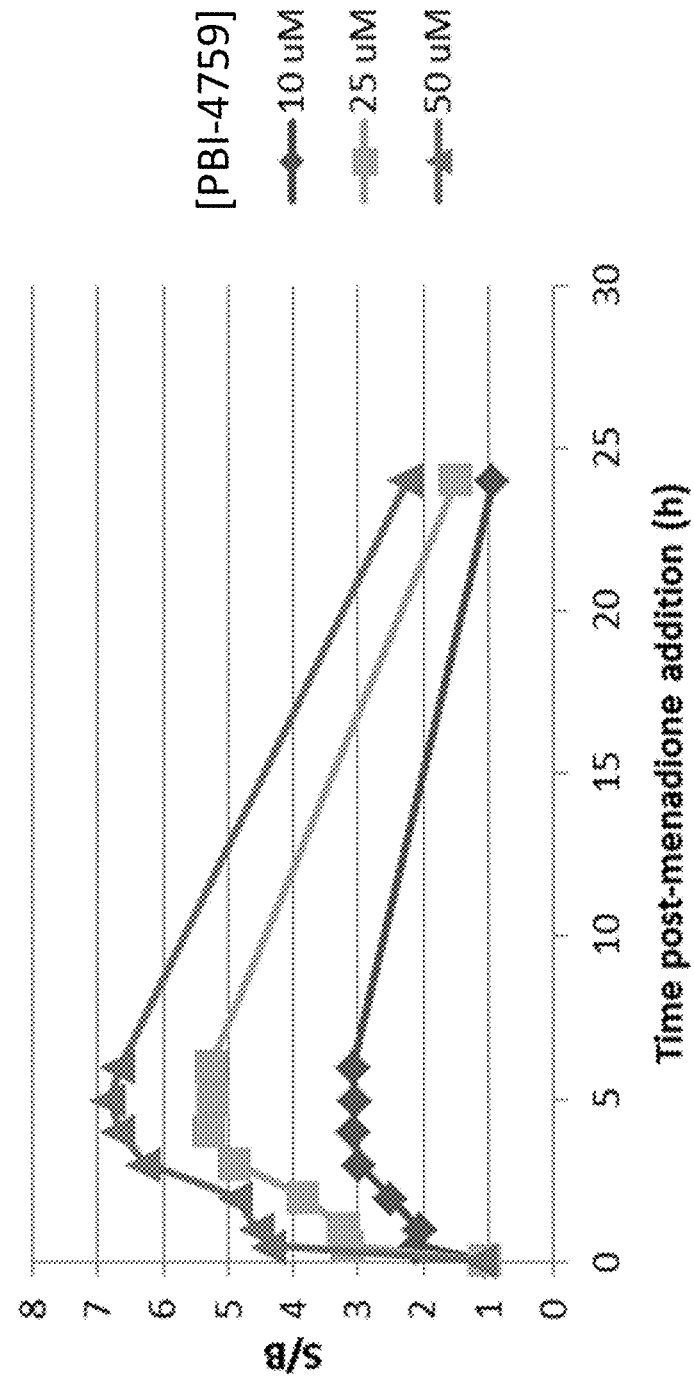
FIG. 25 illustrates the real-time monitoring of reactive oxygen species (ROS) in A549 cells using the method described herein comprising a NANOLUC luciferase protein sensor and a pro-furimazine hydrogen peroxide substrate (PBI-4759).

The results demonstrate that the method described herein can be used to monitor in real-time caspase activation (FIG. 25).

Example 22: Real-Time Monitoring of Reactive Oxygen Species (ROS)

A549 cells were plated at 1,000 cells/well into wells of a 384-well plate and incubated overnight. Then, either 10, 25, or 50 µM of a pro-furimazine hydrogen peroxide substrate, PBI-4759, and 40 ng/ml NANOLUC luciferase protein sensor were added to the cells. Menadione (200 µM), a known ROS inducer, or a vehicle control (DMSO) was added to the cells. Luminescence was monitored over time using a Tecan M1000 plate reader. As menadione-induced hydrogen peroxide production in cells, the increase in luminescence above background was measured, and the maximum signal was reached at 5 hours after addition of menadione.

Figure 26:
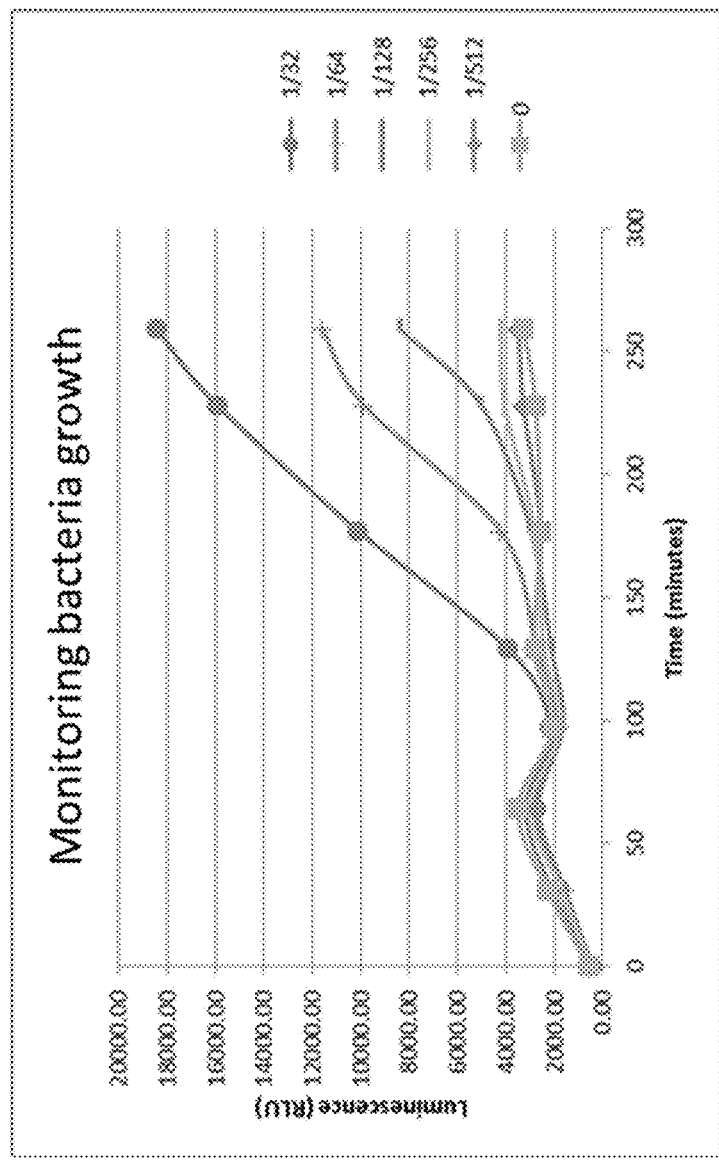
FIG. 26 illustrates the real-time monitoring of bacterial growth using the method described herein.

The results demonstrate that the method described herein can be used to monitor in real-time reactive oxygen species (FIG. 26).

Example 23: Using the Method Described Herein in Bacteria Cells

*Escherichia coli* (ATCC25922) were grown at 37° C. overnight. The overnight culture was then diluted 50-fold in fresh media and incubated for several hours to reach log phase. Samples of the culture were serially diluted in media into wells of a 96-well plate in the presence of 40 ng/ml NANOLUC luciferase protein sensor and 50 µM PBI-4600 pro-substrate (dilution factors "1/32, 1/64, etc."). The bacterial growth was measured by monitoring increase in bioluminescence at multiple time points using the Tecan M1000 plate reader.

The results show that the method described herein can be used with live bacterial cells to monitor their growth in real-time (FIG. 27).

Example 24: Monitoring Cell Viability in Tissue

Tissue samples are perfused with PBS containing heparin to remove blood and clots, and the weight determined. Approximately 10 mg of tissue is homogenized in 1-2 ml PBS containing 2 mM EDTA. The tissue extract is centrifuged, and the supernatant collected. The tissue extract is titrated into wells of a 96-well plate along with 50 µM PBI-4600 and 40 ng/ml NANOLUC luciferase enzyme. Luminescence is measured at various time points using a plate reader luminometer.

---

The invention claimed is:

1. A method comprising:
   (a) providing extracellularly to a cell:
      (i) a luciferase enzyme, wherein the luciferase enzyme generates a detectable luminescent signal upon interaction with a substrate selected from furimazine, coelenterazine, or luciferin, and wherein the luciferase enzyme is incapable of entering the cell; and
      (ii) a pro-substrate comprising a substrate moiety and a blocking moiety that is capable of entering the cell, wherein the pro-substrate is selected from pro-furimazine, pro-coelenterazine, and pro-luciferin substrate, wherein interaction of the pro-substrate with an intracellular enzyme that cleaves the blocking moiety from the substrate moiety thereby converting the pro-substrate into the substrate for the luciferase enzyme, wherein the substrate is capable of exiting the cell; and
   (b) detecting the detectable luminescent signal generated by the interaction of the substrate and the luciferase enzyme, wherein real-time magnitude of the luminescent detectable signal correlates with the real-time intracellular amount of the intracellular enzyme.

2. The method of claim 1, wherein the detecting the detectable luminescent signal comprises real-time monitoring of the detectable luminescent signal.

3. The method of claim 1, wherein the pro-substrate is stable in the absence of interaction with the intracellular enzyme and continuously enters the cell.

4. The method of claim 1, wherein substantially all of the substrate generated by interaction of the pro-substrate with the intracellular enzyme is either utilized by the luciferase enzyme or otherwise degraded such that the substrate does not accumulate extracellularly.

5. The method of claim 1, wherein the detectable luminescent signal generated by the interaction of the substrate and the luciferase enzyme only persists when substrate is continually produced by interaction of the pro-substrate with the intracellular enzyme, and wherein increases and decreases in the intracellular concentration of the intracellular enzyme result in corresponding increases and decreases in the detectable luminescent signal generated by the interaction of the substrate and the luciferase enzyme.

6. The method of claim 1, wherein the detectable luminescent signal is a non-accumulated, real-time signal.

7. The method of claim 1, wherein the cell is not engineered to express the luciferase enzyme.

8. The method of claim 1, wherein the luciferase enzyme retains activity over the time scale of the detecting.

9. The method of claim 1, wherein the luciferase enzyme comprises an *Oplophorus*, beetle, *Renilla* or *Gaussia* luciferase.

10. The method of claim 9, wherein the luciferase enzyme comprises an *Oplophorus* luciferase with enhanced protein stability, enhanced bioluminescence, and/or enhanced signal stability.

* * * * *